United States Patent
Park et al.

(10) Patent No.: US 11,443,429 B2
(45) Date of Patent: Sep. 13, 2022

(54) ATLAS REGISTRATION FOR RESTING STATE NETWORK MAPPING IN PATIENTS WITH BRAIN TUMORS

(71) Applicants: Ki Yun Park, St. Louis, MO (US); Abraham Snyder, St. Louis, MO (US); Eric Leuthardt, St. Louis, MO (US)

(72) Inventors: Ki Yun Park, St. Louis, MO (US); Abraham Snyder, St. Louis, MO (US); Eric Leuthardt, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 16/889,192

(22) Filed: Jun. 1, 2020

(65) Prior Publication Data

US 2020/0380681 A1    Dec. 3, 2020

Related U.S. Application Data

(60) Provisional application No. 62/854,795, filed on May 30, 2019.

(51) Int. Cl.
*G06K 9/00* (2022.01)
*G06T 7/00* (2017.01)
(Continued)

(52) U.S. Cl.
CPC .......... *G06T 7/0014* (2013.01); *A61B 5/0042* (2013.01); *A61B 5/0263* (2013.01);
(Continued)

(58) Field of Classification Search
CPC ....... G06T 7/0014; G06T 3/0093; G06T 7/30; G06T 2207/10088; G06T 2207/30016; G06T 2207/30096; G06T 2207/20128; G06T 7/149; G06T 7/11; G06T 7/0012; A61B 5/055; A61B 5/0263; A61B 5/0042; A61B 2576/026; G01R 33/5616; G01R 33/5608; G01R 33/4806
(Continued)

(56) References Cited

U.S. PATENT DOCUMENTS 7,215,122 B2    5/2007   Zhao et al.
7,469,159 B2   12/2008   Deyoe et al.
(Continued)

OTHER PUBLICATIONS

Damoiseaux et al., "Reduced resting-state brain activity in the "default network" in normal aging", Cerebral Cortex, Aug. 2008, pp. 1856-1864, vol. 18.
(Continued)

*Primary Examiner* — Van D Huynh
(74) *Attorney, Agent, or Firm* — Armstrong Teasdale LLP

(57) ABSTRACT

A method for mapping brain function of a subject includes generating a lesion mask using a search light algorithm based on a plurality of anatomical images of the subject. The plurality of anatomical images are registered with atlas images by nonlinear atlas registration using the generated lesion mask to generate a warping map. A plurality of functional images of the subject are resampled using the warping map to generate a functional map, functional connectivity is computed using the functional map and a multi-layer perceptron.

20 Claims, 18 Drawing Sheets
(15 of 18 Drawing Sheet(s) Filed in Color)

(51) Int. Cl.

| | |
|---|---|
| *A61B 5/055* | (2006.01) |
| *A61B 5/026* | (2006.01) |
| *A61B 5/00* | (2006.01) |
| *G06T 3/00* | (2006.01) |
| *G06T 7/30* | (2017.01) |

(52) U.S. Cl.
CPC ............ *A61B 5/055* (2013.01); *G06T 3/0093* (2013.01); *G06T 7/30* (2017.01); *G06T 2207/10088* (2013.01); *G06T 2207/30016* (2013.01); *G06T 2207/30096* (2013.01)

(58) Field of Classification Search
USPC ........................................................ 382/128
See application file for complete search history.

(56) References Cited

U.S. PATENT DOCUMENTS

| | | | |
|---|---|---|---|
| 7,715,901 | B2 | 5/2010 | Salomon et al. |
| 7,729,755 | B2 | 6/2010 | Laken |
| 7,894,903 | B2 | 2/2011 | John et al. |
| 8,116,575 | B1* | 2/2012 | Saisan ................... G06K 9/6284 382/160 |
| 9,480,402 | B2 | 11/2016 | Leuthardt et al. |
| 10,357,181 | B2* | 7/2019 | Morimoto ............. A61B 5/4064 |
| 2003/0229107 | A1 | 12/2003 | Cowan et al. |
| 2004/0096089 | A1* | 5/2004 | Borsook ................ A61B 5/055 382/131 |
| 2006/0074336 | A1* | 4/2006 | Grieve ................... A61B 5/369 600/544 |
| 2007/0010732 | A1 | 1/2007 | Deyoe et al. |
| 2008/0292194 | A1* | 11/2008 | Schmidt ................. G06T 7/143 382/131 |
| 2009/0012386 | A1 | 1/2009 | Buckner |
| 2009/0253982 | A1 | 10/2009 | Wang |
| 2013/0123607 | A1* | 5/2013 | Leuthardt ............ A61B 5/0022 600/407 |
| 2016/0239969 | A1* | 8/2016 | Davatzikos .......... G06K 9/6247 |
| 2017/0281112 | A1* | 10/2017 | Pack ..................... G06T 11/005 |

OTHER PUBLICATIONS

Dosenbach et al. "Distinct brain networks for adaptive and stable task control in humans", Proceedings of the National Academy of Sciences USA, 2007, pp. 11073-11078; vol. 104; No. 26.

Dosenbach et al., "A Core System for the Implementation of Task Sets", Neuron, 2006, pp. 799-812, vol. 50.

Dosenbach et al., "A dual-networks architecture of top-down control", Trends in Cognitive Sciences, 2008, pp. 99-105, vol. 12, No. 3.

Doucet et al., "Brain activity at rest: a multiscale hierarchical functional organization", Journal of Neurophysiology, 2011, pp. 2753-2763, vol. 105.

Dunmar et al., "Learning and Generalization in a Linear Perceptron Stochastically Trained with Noisy Data" Journal of Physics A: Mathematical and General, 1993, pp. 5767-5779, vol. 26, No. 21.

Fair et al., "Functional brain networks develop from a "local to distributed" organization", PLoS Computational Biology, 2009, 14 pages, vol. 5, No. 5.

Fox et al., "The human brain is intrinsically organized into dynamic, anticorrelated functional networks", Proceedings of the National Academy of Sciences USA, 2005, pp. 9673-9678; vol. 102; No. 27.

Fox et al., "The global signal and observed anticorrelated resting state brain networks", Journal of Neurophysiology, 2009, vol. 101, pp. 3270-3283.

Fox et al., "Spontaneous neuronal activity distinguishes human dorsal and ventral attention systems", Proceedings of the National Academy of Sciences USA, 2006, pp. 10046-10051, vol. 103, No. 26.

Fox et al., "Clinical applications of resting state functional connectivity", Frontiers in Systems Neuroscience, 2010, 13 pages, vol. 4, Article 19.

Fox et al., "Spontaneous fluctuations in brain activity observed with functional magnetic resonance imaging", Nature Reviews Neuroscience, 2007, pp. 700-711, vol. 8.

Ganmor et al., "Sparse low-order interaction network underlies a highly correlated and learnable neural population code", Proceedings of the National Academy of Sciences USA, 2011, pp. 9679-9684, vol. 108, No. 23.

Gaona et al., "Nonuniform High-Gamma (60-500 Hz) Power Changes Dissociate Cognitive Task and Anatomy in Human Cortex", The Journal of Neuroscience, 2011, pp. 2091-2100, vol. 31, No. 6.

Geman et al., "Stochastic relaxation, gibbs distributions, and the bayesian restoration of images", IEEE Transactions on Pattern Analysis and Machine Intelligence, 1984, pp. 721-741, vol. PAMI-6, No. 6.

Guimera et al., "Cartography of complex networks; modules and universal roles", Journal of Statistical Mechanics Theory and Experiment, 2005, 17 pages.

Hampson et al., "Connectivity-behavior analysis reveals that functional connectivity between left BA39 and Broca's area varies with reading ability", NeuroImage, 2006, pp. 513-519, vol. 31.

He et al., "Breakdown of functional connectivity in frontoparietal networks underlies behavioral deficits in spatial neglect", Neuron, 2007, pp. 905-918, vol. 53.

He et al., "Electrophysiological correlates of the brain's intrinsic large-scale functional architecture", Proceedings of the National Academy of Sciences USA, 2008, pp. 16038-16044, vol. 105, No. 41.

Hickok et al., "Dorsal and ventral streams: a framework for understanding aspects of the functional anatomy of anguage", Cognition, 2004, pp. 67-99, vol. 92.

Hill et al., "Similar patterns of cortical expansion during human development and evolution", Proceedings of the National Academy of Sciences USA, 2010, 6 pages.

Hornik et al., "Multilayer Feedforward Networks Are Universal Approximators", Neural Networks, 1989, pp. 359-366, vol. 2.

Kahn et al., "Distinct cortical anatomy linked to subregions of the medial temporal lobe revealed by intrinsic functional connectivity", Journal of Neurophysiology, 2008, pp. 129-139, vol. 100.

Kincade et al., "An event-related functional magnetic resonance imaging study of voluntary and stimulus-driven prienting of attention", The Journal of Neuroscience, 2005, pp. 4593-4604, vol. 25, No. 18.

Kirkpatrick, "Optimization by Simulated Annealing: Quantitative Studies", Journal of Statistical Physics, 1984, pp. 975-986, vol. 34, Nos. 5/6.

Kirkpatrick et al., "Optimization by Simulated Annealing", Science, 1983, pp. 671-680, vol. 220, No. 4598.

Kupinski et al., "Experimental determination of object statistics from noisy images", Journal of the Optical Society of America A: Optics, Image Science, and Vision, 2003, pp. 421-429, vol. 20, No. 3.

Lecun et al., "Handwritten Digit Recognition: Applications of Neural Network Chips and Automatic Learning", IEEE Communications Magazine, 1989, pp. 41-46.

Lecun et al., "Backpropagation Applied to Handwiillen Zip Code Recognition" Neural Computation, 1989, pp. 541-551, vol. 1.

Lee et al., "Clustering of resting state networks", PLoS One, 2012, 12 pages, vol. 7, No. 7.

Lemm et al., "Introduction to machine learning for brain imaging", NeutroImage, 2011, pp. 387-399, vol. 56.

Lippmann, "Pattern-Classification Using Neural Networks" IEEE Communications Magazine, 1989, pp. 47-64.

Lippmann, "Review of Neural Networks for Speech Recognition", Neural Computation, 1989, pp. 1-38, vol. 1.

Logethetis et al. "Interpreting the BOLD signal", Annual Review of Physiology, 2004, pp. 735-769, vol. 66.

Marrelec et al., "Regions, systems, and the brain: Hierarchical measures of functional integration in fMRI", Medical Image Analysis, 2008, pp. 484-496, vol. 12.

(56) References Cited

OTHER PUBLICATIONS

Marrelec et al., "Assessing the influence of different ROI selection strategies on functional connectivity analyses of fMRI data acquired during steady-state conditions", PLoS One, 2011, 14 pages, vol. 6, No. 4.
Mennes et al., "Inter-individual differences in resting-state functional connectivity predict task-induced BOLD activity", NeuroImage, 2010, pp. 1690-1701, vol. 50.
Fair et al., A Method for Using Cloked and Event-Related FMRI Data To Study "Resting State" Functional Connectivity, Neuroimage, Mar. 2007; 35, 1, pp. 396-405.
Smith et al., Correspondence of the Brain's Functional Architecture During Activation and Rest, PNAS, Aug. 4, 2009, vol. 106, No. 31, pp. 13040-13045, with supporting information, Smith et al., 1073/pnas,0905267, pp. 1-10.
Goldman et al., (Simultaneous EEG and fMRI of the alph rhythm, Neuroreport, Dec. 20, 2002, vol. 13, No. 18, pp. 2487-2492.
Meunier et al., "Modular and hierarchically modular organization of brain networks", Frontiers in Neuroscience, 2010, 11 pages, vol. 4, Article 200.
Miller et al., "Direct electrophysiological measurement of human default network areas", Proceedings of the National Academy of Sciences USA, 2009, pp. 12174-12177, vol. 106, No. 29.
Muller et al., "An Introduction to Kernel-Based Learning Algorithms", IEEE Transactions on Neural Networks, 2001, pp. 181-201, vol. 12, No. 2.
Murphy et al., "The impact of global signal regression on resting state correlations: are anti-correlated networks introduced?", NeuroImage, 2009, pp. 893-905, vol. 44, No. 3.
Petacchi et al., "Cerebellum and auditory function: an ALE meta-analysis of functional neuroimaging studies", Human Brain Mapping, 2005, pp. 118-128, vol. 25.
Petersen et al., "Positron emission tomographic studies of the cortical anatomy of single-word processing", Nature, 1988, pp. 585-589, vol. 331.
Plaut et al., "Experiments on Learning by Back Propagation", Technical Report CMU-CS-86-126, 1986, 45 pages.
Power et al., "Spurious but systematic correlations in functional connectivity MRI networks arise from subject motion", NeuroImage, 2012, pp. 2142-2154, vol. 59.
Power et al., "Functional network organization of the human brain", Neuron, 2011, pp. 665-678, vol. 72.
Pravata et al., "Functional connectivity MR imaging of the language network in patients with drug-resistant epilepsy", American Journal of Neuroradiology, 2011, pp. 532-540, vol. 32.
Rosenblatt, "The perceptron: a probabilistic model for information storage and organization in the brain", Psychological Review, 1958, pp. 386-408, vol. 65, No. 6.
Rumelhart et al., "Learning representations by back-propagating errors", Nature, 1986, pp. 533-536, vol. 323.
Sestieri et al., "Episodic memory retrieval, parietal cortex, and the default mode network: functional and topographic analyses", The Journal of Neuroscience, 2011, pp. 4407-4420, vol. 31, No. 12.
Sestieri et al., "Attention to memory and the environment: functional specialization and dynamic competition in human posterior parietal cortex", The Journal of Neuroscience, 2010, pp. 8445-8456, vol. 30, No. 25.
Shulman et al., "Right hemisphere dominance during spatial selective attention and target detection occurs outside the dorsal frontoparietal network", The Journal of Neuroscience, 2010, pp. 3640-3651, vol. 30, No. 10.
Shulman et al., "Interaction of stimulus-driven reorienting and expectation in ventral and dorsal frontoparietal and basal ganglia-cortical networks", The Journal of Neuroscience, 2009, pp. 4392-4407, vol. 29, No. 14.
Smith et al., "Correspondence of the brain's functional architecture during activation and rest", Proceedings of the National Academy of Sciences USA, 2009, pp. 13040-13045, vol. 106, No. 31.
Smyser et al., "Longitudinal Analysis of Neural Network Development in Preterm Infants", Cerebral Cortex, 2010, pp. 2852-2862, vol. 20, No. 285.
Simon "Near-decomposability and complexity: How a mind resides in a brain", The Mind, the Brain, and Complex Adaptive Systems, 1995, pp. 25-43.
Spoormaker et al., "Development of a large-scale functional brain network during human non-rapid eye movement sleep", The Journal of Neuroscience, 2010, pp. 11379-11387, vol. 30, No. 34.
Spreng, "The fallacy of a "task-negative" network", Frontiers in Psychology, 2012, pp. 1-5, vol. 3, Article 145.
Sylvester et al., "Anticipatory suppression of nonattended locations in visual cortex marks target location and predicts perception", The Journal of Neuroscience, 2008, pp. 6549-6556, vol. 28, No. 26.
Sylvester et al., "Asymmetry of anticipatory activity in visual cortex predicts the locus of attention and perception", The Journal of Neuroscience, 2007, pp. 14424-14433, vol. 27, No. 52.
Sylvester et al., "Anticipatory and stimulus-evoked blood oxygenation level-dependent modulations related to spatial attention reflect a common additive signal", The Journal of Neuroscience, 2009, pp. 10671-10682, vol. 29, No. 34.
Tomasi et al., "Language network: segregation, laterality and connectivity", Molecular Psychiatry, 2012, No. 17.
Tosoni et al., "Distinct representations for shifts of spatial attention and changes of reward contingencies in the human brain", Cortex, 2012, pp. 1-17.
Van Essen et al., "An integrated software suite for surface-based analyses of cerebral cortex", Journal of the American Medical Informatics Association, 2001, pp. 443-459; vol. 8, No. 5.
Van Essen et al. "A Population-Average, Landmark-and Surface-based (PALS) Atlas of Human Cerebral Cortex", NeuroImage, 2005, pp. 635-662, vol. 28.
Van Dijk et al., "Intrinsic functional connectivity as a tool for human connectomics: theory, properties, and optimization", Journal of Neurophysiology, 2010, pp. 297-321, vol. 103.
Walther et al., "Simple line drawings suffice for functional MRI decoding of natural scene categories", Proceedings of the National Academy of Sciences USA, 2010, pp. 9661-9666, vol. 108, No. 23.
Xu et al., "The influence of carbon dioxide on brain activity and metabolism in conscious humans", Journal of Cerebral Blood Flow & Metabolism, 2011, pp. 58-67, vol. 31.
Yeo et al., "The organization of the human cerebral cortex estimated by intrinsic functional connectivity", Journal of Neurophysiology, 2011, 137 pages.
Zhang et al., "Intrinsic functional relations between cerebral cortex and thalamus", Journal of Neurophysiology, 2008, pp. 1740-1748, vol. 100.
Astafiev et al., "Extrastriate body area in human occipital cortex responds to the performance of motor actions", Nature Neuroscience, 2004, pp. 542-548; vol. 7.
Barrett et al., "Objective assessment of image quality. III. ROC metrics, ideal observers, and likelihood-generating functions", Journal of the Optical Society of America A: Optics, Image Science, and Vision, 1998, pp. 1520-1535, vol. 15.
Beckman et al., "Investigations into resting-state connectivity using independent component analysis", Philosophical transactions of the Royal Society of London Series B, 2005, pp. 1001-1013, vol. 360.
Binder et al., "Mapping anterior temporal lobe language areas with FMRI: a multicenter normative study", NeuroImage, 2011, pp. 1465-1475; vol. 54, No. 2.
Biswal et al., "Functional connectivity in the motor cortex of resting human brain using echo-planer MRI", Magnetic Resonance Medicine, 1995, pp. 537-541, vol. 34, No. 4.
Boly et al.; "Hierarchical clustering of brain activity during human nonrapid eye movement sleep", Proceedings of the National Academy of Sciences USA, 2012, pp. 5856-5861, vol. 109, No. 15.
Briganti et al., "Reorganization of Functional Connectivity of Language Network in Patients with Brain Gliomas", American Journal of neuroradiology, 2012, pp. 1-8.
Buckner, "The serendipitous discovery of the brain's default network", NeuroImage, 2012, pp. 1137-1145, vol. 62.

(56) References Cited

OTHER PUBLICATIONS

Buckner et al., "The organization of the human cerebellum estimated by intrinsic functional connectivity", Journal of Neurophysiology, 2011, pp. 2322-2345, vol. 106.

Corbetta et al., "Voluntary orienting is dissociated from target detection in human posterior parietal cortex", Nature Neuroscience, 2000, pp. 292-297, vol. 3, No. 3.

Dale et al., "Cortical surface-based analysis. I. Segmentation and surface reconstruction", NeuroImage, 1999, pp. 179-194; vol. 9.

Damoiseaux et al., "Consistent resting-state networks across healthy subjects", Proceedings of the National Academy of Sciences USA, 2006, pp. 13848-13853; vol. 103; No. 37.

Damoiseaux et al., "Greater than the sum of its parts; a review of studies combining structural connectivity and resting-state functional connectivity", Brain Structure & Function, 2009, pp. 525-533, vol. 213.

* cited by examiner

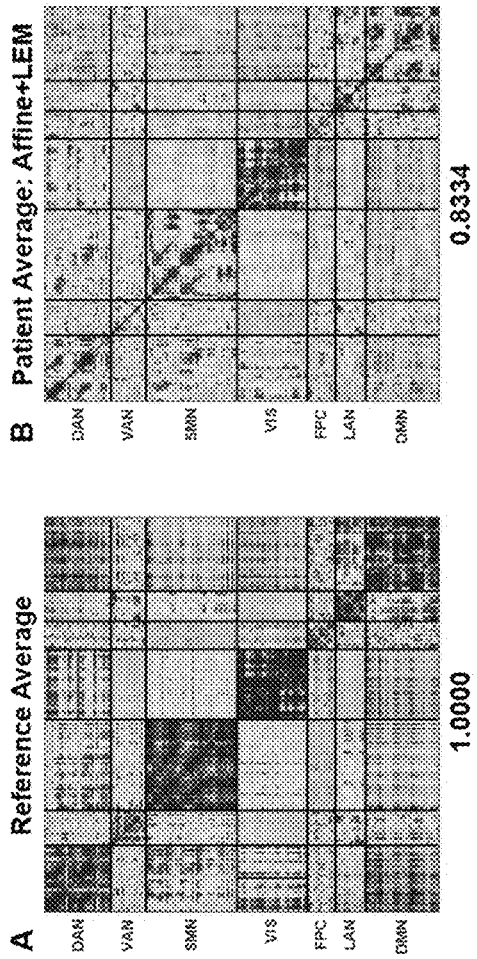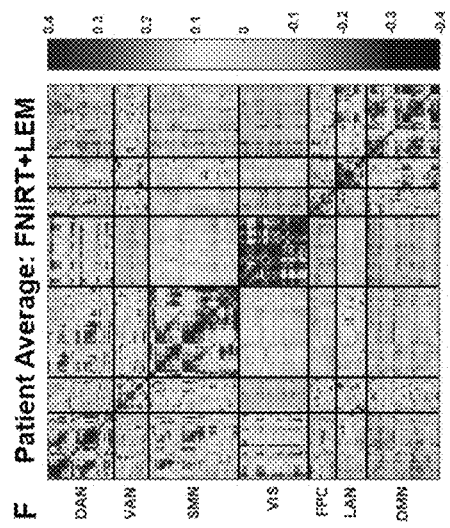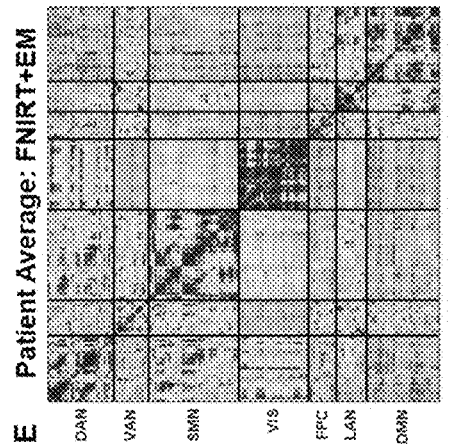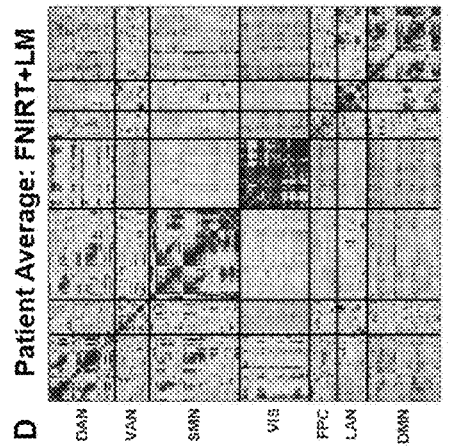
FIG. 5A  FIG. 5B  FIG. 5C  FIG. 5D  FIG. 5E  FIG. 5F

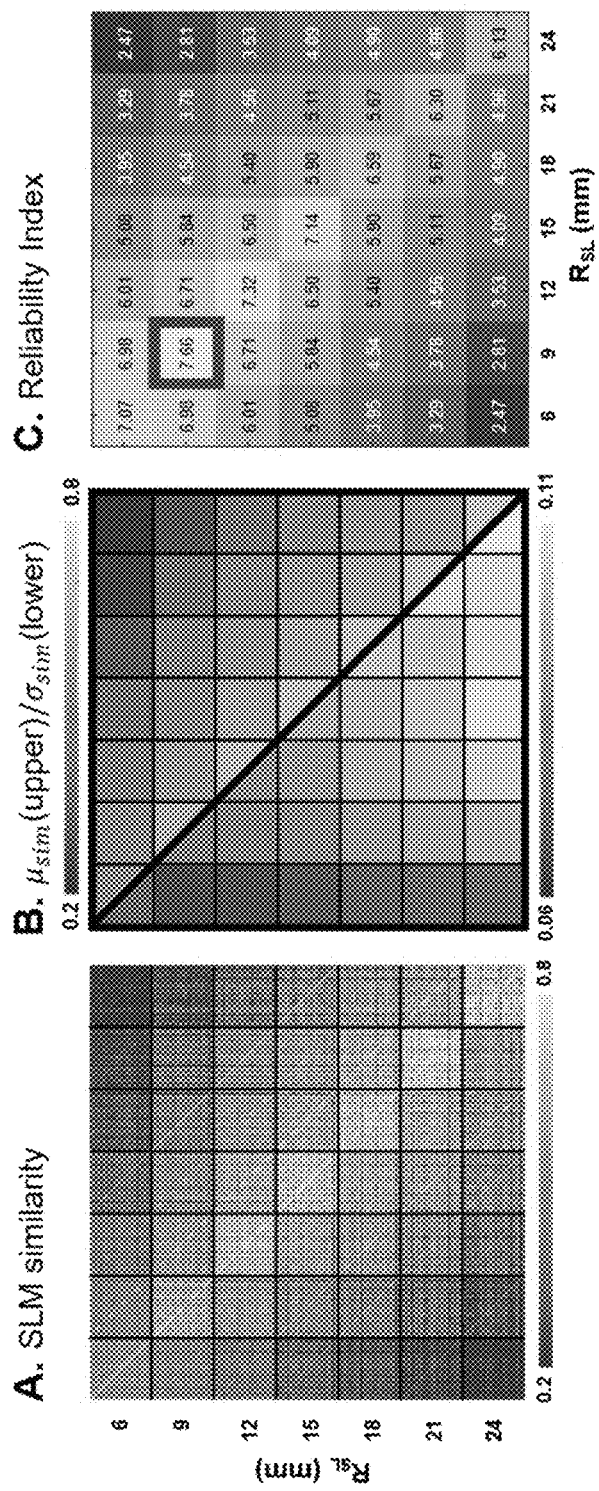

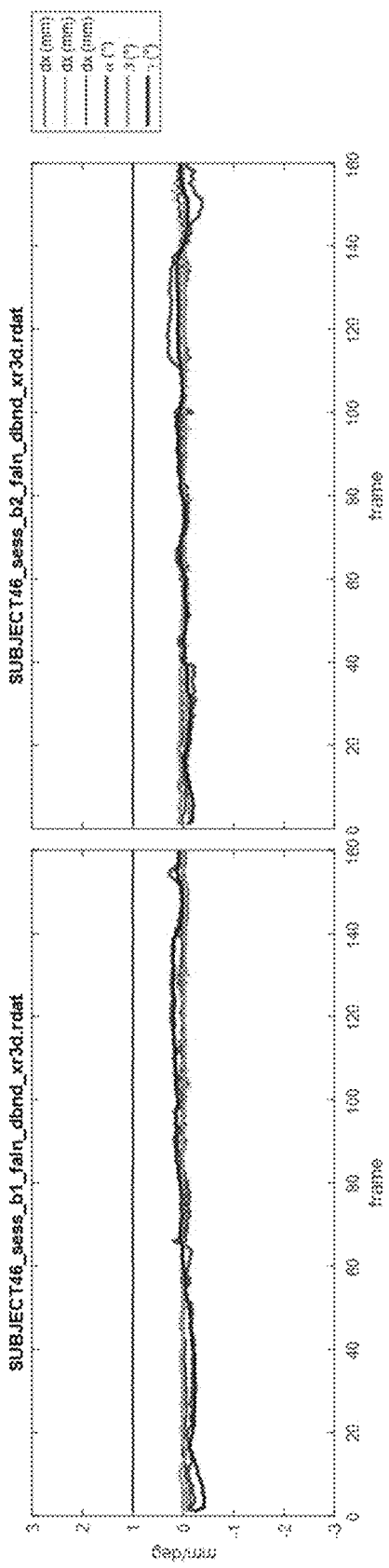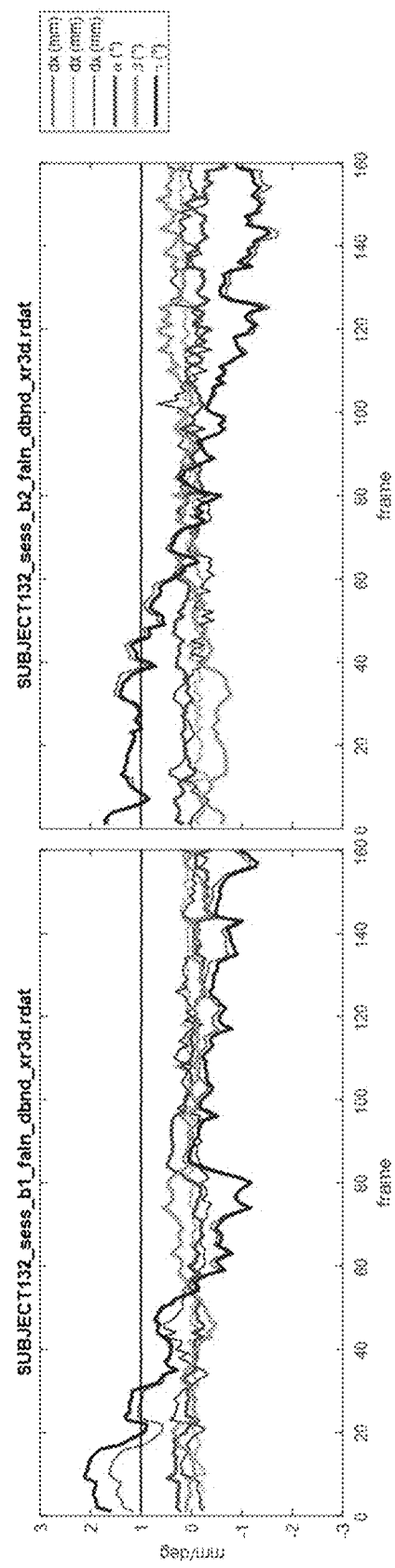
FIG. 14A
FIG. 14B
FIG. 14C
FIG. 14D

ATLAS REGISTRATION FOR RESTING STATE NETWORK MAPPING IN PATIENTS WITH BRAIN TUMORS

CROSS REFERENCE TO RELATED APPLICATION

This application claims priority to U.S. provisional application No. 62/854,795 filed May 30, 2019, which is incorporated herein in its entirety.

STATEMENT REGARDING FEDERALLY SPONSORED RESEARCH & DEVELOPMENT

This invention was made with government support under CA203861 awarded by the National Institutes of Health. The government has certain rights in the invention.

FIELD

The field of this disclosure relates generally to brain mapping systems and, more particularly, to systems and methods for atlas registration for resting state network mapping in patients with brain tumors.

BACKGROUND

Presurgical non-invasive localization of function in patients with brain tumors may improve functional outcomes by informing the surgical approach. However, pre-surgical mapping can be challenging in patients with large tumors owing to mass effect.

Preoperative mapping of function provides neurosurgeons a means of planning an operative approach to tumor resection that maximally preserves function, at least in principle. Preserved function as well as maximal resection both have been cited as predictors of long-term survival. Classically, functional mapping has been achieved intra-operatively by direct cortical stimulation (DCS); this technique currently remains a clinical gold standard. However, localization of function with functional magnetic resonance imaging (fMRI) is non-invasive and can be accomplished prior to surgery. In view of these advantages, use of fMRI for pre-surgical functional mapping is steadily increasing. Moreover, fMRI can be used in cases where DCS fails.

Task-based fMRI offers a natural means of localizing function. Most commonly, finger tapping and word generation are used to map the representation of motor and language functions, respectively. However, task-based fMRI depends on the patient's capacity to comply with the paradigm, which often is compromised. Resting state fMRI (rs-fMRI) is an alternative strategy that does not depend on patient compliance. In 1995, Biswal and colleagues demonstrated that infra-slow (<0.1 Hz) spontaneous fluctuations of blood oxygen level dependent (BOLD) are correlated within the somatomotor system. Since then, this basic finding has been extended to multiple functional systems spanning the entire brain. Thus, fMRI time series can be extracted from seed regions placed anywhere within the brain. The topographies imaged by rs-fMRI currently are known as resting state networks (RSNs). RSNs are visualized by computing temporal correlations between the seed and all other voxels. rs-fMRI can be performed in awake, asleep, and even lightly sedated patients. It is now well established that RSNs topographically correspond to fMRI responses elicited by a wide variety of behavioral paradigms. Hence, rs-fMRI is increasingly used to localize function in the context of pre-neurosurgical planning.

At least some known methods and systems perform pre-surgical functional mapping using a multi-layer perceptron (MLP) trained to assign RSN affiliation to rs-fMRI functional connectivity maps corresponding to all brain voxels. Thus, MLP-based RSN mapping exemplifies supervised classification. In contrast, spatial independent component analysis (sICA), the major alternative to seed-based correlation mapping, exemplifies unsupervised classification. Because it is a supervised classifier, the MLP is capable of generating reliable RSN maps in individuals. MLP-based RSN mapping has demonstrated effectiveness in the context of pre-surgical planning. Importantly, however, accurate RSN mapping depends on precise structural normalization of individual brains to a standard atlas template. Structural normalization is a non-trivial challenge in patients with brain tumors owing to destruction of normal anatomy and mass effect from swelling or edema.

The first addressed question concerns atlas registration of structural images. Affine atlas registration incompletely eliminates patient-specific anatomical differences but is relatively robust to the effects of lesions. Nonlinear atlas registration (warping) effectively reduces individual anatomic differences in normal subjects but may not be stable in the presence of distorted anatomy. Non-linear warping can be stabilized by cost-function masking (CFM), that is, excluding the lesion from the voxel similarity measure. The value of CFM has been established, notwithstanding initial objections. Importantly, however, CFM depends on prior segmentation of the lesion. Since a reliable automated procedure to accomplish this operation presently does not exist, conventional CFM is labor intensive.

This Background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

BRIEF DESCRIPTION

In one aspect, a method for mapping brain function of a subject includes generating a lesion mask using a search light algorithm based on a plurality of anatomical images of the subject. The plurality of anatomical images are registered with atlas images by nonlinear atlas registration using the generated lesion mask to generate a warping map. A plurality of functional images of the subject are resampled using the warping map to generate a functional map, functional connectivity is computed using the functional map and a multi-layer perceptron.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 5A, 5B, 5C, 5D, 5E, and 5F are functional connectivity matrices averaged over 20 patients.

FIGS. 8A, 8B, and 8C graphically present SL radius optimization based on computed reliability index.

FIGS. 14A, 14B, 14C, and 14D are graphs of representative translation and rotation realignment parameters calculated in patients with low movement (FIGS. 14A and 14B) and high movement (FIGS. 14C and 14D).

Like reference symbols in the various drawings indicate like elements.

DETAILED DESCRIPTION OF THE DRAWINGS

The exemplary systems, apparatus, and methods described herein overcome at least some known disadvantages associated with at least some known atlas registration and brain mapping techniques. A searchlight (SL) algorithm semi-automates the process of generating a lesion mask. The SL algorithm identifies structurally abnormal regions in the brain by computing a local spatial correlation map (i.e., SL image). Tumor exclusion masks then are generated by binarization and post-processing of the SL image. The ultimate objective is to optimize functional mapping in patients with brain tumors. The example embodiments may use affine or non-linear atlas registration and various masking options. The embodiments generally provide improved results over at least some known systems and methods.

Figure 16:
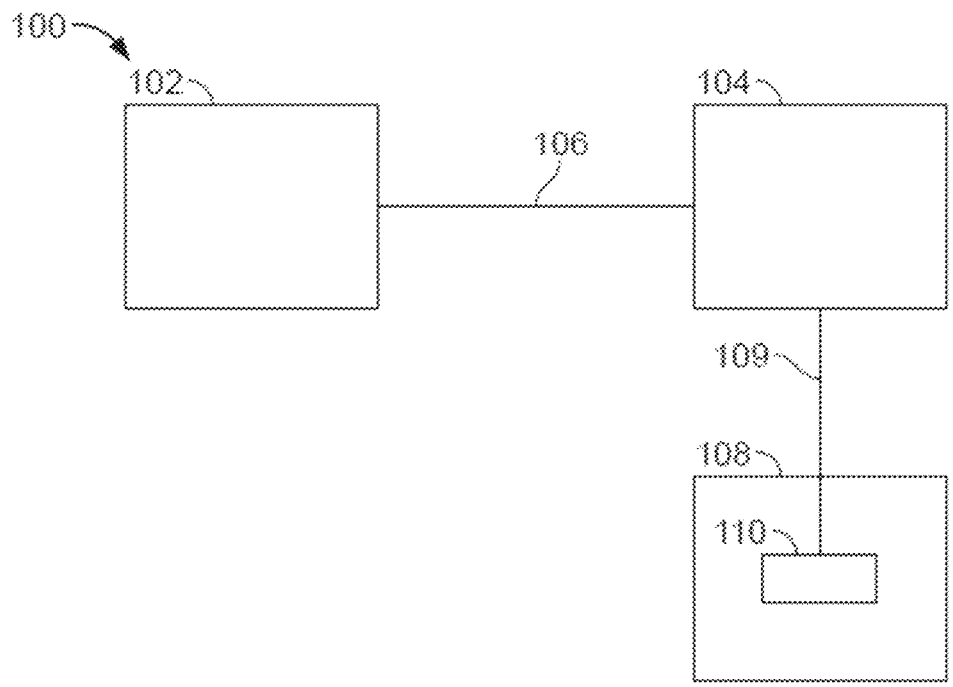
FIG. 16 is a block diagram of an exemplary system for task-less mapping of brain activity.

FIG. 16 illustrates an exemplary system 100 for mapping brain activity of a subject (not shown). It should be noted that the term "brain activity" as used herein includes the various activities within a brain of the subject that correspond to various tasks performed by the subject. For example, the brain transmits and receives signals in the form of hormones, nerve impulses, and chemical messengers that enable the subject to move, eat, sleep, and think. In the exemplary embodiment, system 100 is used to identify locations within a plurality of networks within the brain that are responsible for such brain activities.

As seen in FIG. 16, system 100 includes a sensing system 102 that is configured to detect a plurality of measurements of brain activity that is representative of at least one parameter of the brain of the subject during a resting state. In one suitable embodiment, sensing system 102 is a magnetic resonance imaging device (MRI) that is configured to generate at least one spectroscopic signal representative of a plurality of measurements of brain activity that is representative of at least one parameter of the brain of the subject during a resting state. More specifically, sensing system 102 may generate an altered magnetic field within the brain to measure various parameters of the brain. In another suitable embodiment, sensing system 102 may be a specialized MRI, such as a functional magnetic resonance imaging (fMRI) device that is used to measure a variation in blood flow (hemodynamic response) related to neural activity in the brain or spinal cord (not shown) of the subject. In yet another suitable embodiment, sensing system 102 may be an electrocorticography device having at least one electrode (not shown) to measure at least one voltage fluctuation within the brain. It should be noted that the present disclosure is not limited to any one particular type of imaging and electrical technique or device, and one of ordinary skill in the art will appreciate that the current disclosure may be used in connection with any type of technique or device that enables system 100 to function as described herein.

In the exemplary embodiment, system 100 also includes a computing device 104 coupled to sensing system 102 via a data conduit 106. It should be noted that, as used herein, the term "couple" is not limited to a direct mechanical, electrical, and/or communication connection between components, but may also include an indirect mechanical, electrical, and/or communication connection between multiple components. Sensing system 102 may communicate with computing device 104 using a wired network connection (e.g., Ethernet or an optical fiber), a wireless communication means, such as radio frequency (RF), e.g., FM radio and/or digital audio broadcasting, an Institute of Electrical and Electronics Engineers (IEEE®) 802.11 standard (e.g., 802.11(g) or 802.11(n)), the Worldwide Interoperability for Microwave Access (WIMAX®) standard, a short-range wireless communication channel such as BLUETOOTH®, a cellular phone technology (e.g., the Global Standard for Mobile communication (GSM)), a satellite communication link, and/or any other suitable communication means. IEEE is a registered trademark of the Institute of Electrical and Electronics Engineers, Inc., of New York, N.Y. WIMAX is a registered trademark of WiMax Forum, of Beaverton, Oreg. BLUETOOTH is a registered trademark of Bluetooth SIG, Inc. of Kirkland, Wash.

In the exemplary embodiment, computing device 104 is configured to receive at least one signal representative of a plurality of measurements of brain activity from sensing system 102. More specifically, computing device 104 is configured to receive at least one signal representative of an altered magnetic field within the brain of the subject from sensing system 102. Alternatively, computing device 104 may be configured to receive at least one signal representative of at least one voltage fluctuation within the brain from at least one electrode.

System 100 also includes a data management system 108 that is coupled to computing device 104 via a network 109. Data management system 108 may be any device capable of accessing network 109 including, without limitation, a desktop computer, a laptop computer, or other web-based connectable equipment. More specifically, in the exemplary embodiment, data management system 108 includes a database 110 that includes previously acquired data of other subjects. In the exemplary embodiment, database 110 can be fully or partially implemented in a cloud computing environment such that data from the database is received from one or more computers (not shown) within system 100 or remote from system 100. In the exemplary embodiment, the previously acquired data of the other subjects may include, for example, a plurality of measurements of brain activity that is representative of at least one parameter of a brain of each of the subjects during a resting state. Database 110 can also include any additional information of each of the subjects that enables system 100 to function as described herein.

Data management system 108 may communicate with computing device 104 using a wired network connection (e.g., Ethernet or an optical fiber), a wireless communication means, such as, but not limited to radio frequency (RF), e.g., FM radio and/or digital audio broadcasting, an Institute of Electrical and Electronics Engineers (IEEE®) 802.11 standard (e.g., 802.11(g) or 802.11(n)), the Worldwide Interoperability for Microwave Access (WIMAX®) standard, a cellular phone technology (e.g., the Global Standard for Mobile communication (GSM)), a satellite communication link, and/or any other suitable communication means. More specifically, in the exemplary embodiment, data management system 108 transmits the data for the subjects to computing device 104. While the data is shown as being stored in database 110 within data management system 108, it should be noted that the data of the subjects may be stored in another system and/or device. For example, computing device 104 may store the data therein.

During operation, while the subject is in a resting state, sensing system 102 uses a magnetic field to align the magnetization of some atoms in the brain of the subject and radio frequency fields to systematically alter the alignment of this magnetization. As such, rotating magnetic fields are produced and are detectable by a scanner (not shown) within sensing system 102. More specifically, in the exemplary embodiment, sensing system 102 detects a plurality of measurements of brain activity that is representative of at least one parameter of the brain of the subject during the resting state. Sensing system 102 also generates at least one spectroscopic signal representative of the plurality of measurements and transmits the signal(s) to computing device 104 via data conduit 106. Moreover, data of other subjects may be transmitted to computing device 104 from database 110 via network 109. As explained in more detail below, computing device 104 produces at least one map, such as a functional connectivity map, for each of the measurements based on a comparison of at least one resting state data point of the subject and a corresponding data point from the previously acquired data set from at least one other subject. Computing device 104 uses the map to categorize or classify the brain activity in a plurality of networks in the brain.

Figure 17:
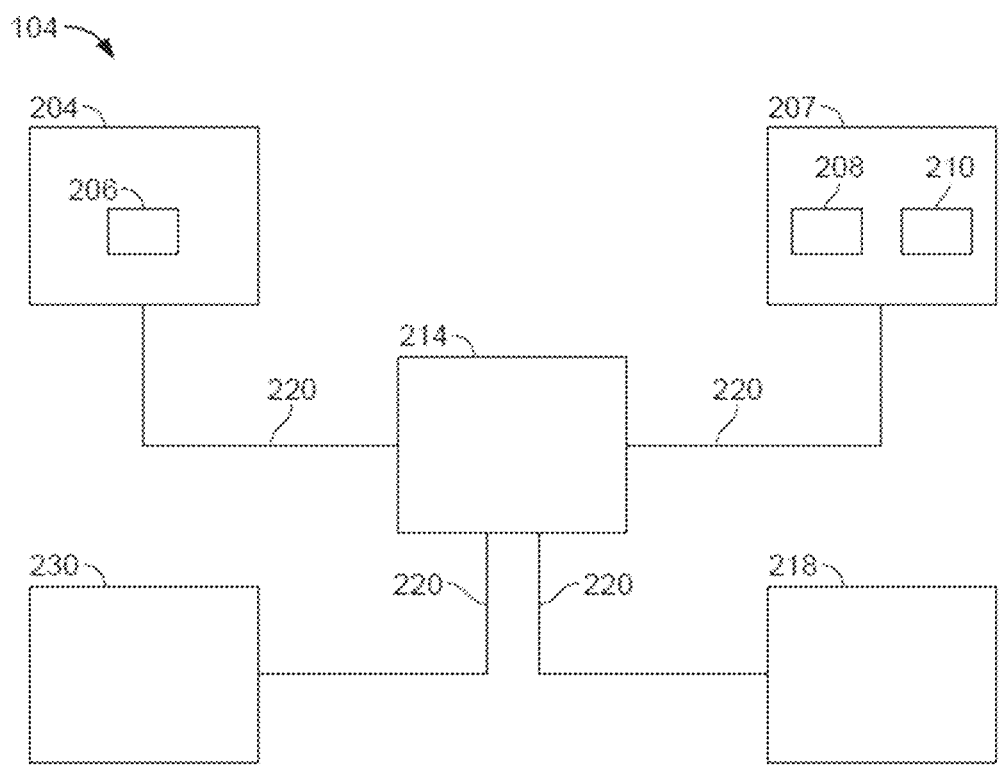
FIG. 17 is a block diagram of an exemplary computing device of the system shown in FIG. 16.

FIG. 17 is a block diagram of computing device 104. In the exemplary embodiment, computing device 104 includes a user interface 204 that receives at least one input from a user, such as an operator of sensing system 102 (shown in FIG. 16). User interface 204 may include a keyboard 206 that enables the user to input pertinent information. User interface 204 may also include, for example, a pointing device, a mouse, a stylus, a touch sensitive panel (e.g., a touch pad, a touch screen), a gyroscope, an accelerometer, a position detector, and/or an audio input interface (e.g., including a microphone).

Moreover, in the exemplary embodiment, computing device 104 includes a presentation interface 207 that presents information, such as input events and/or validation results, to the user. Presentation interface 207 may also include a display adapter 208 that is coupled to at least one display device 210. More specifically, in the exemplary embodiment, display device 210 may be a visual display device, such as a cathode ray tube (CRT), a liquid crystal display (LCD), an organic LED (OLED) display, and/or an "electronic ink" display. Alternatively, presentation interface 207 may include an audio output device (e.g., an audio adapter and/or a speaker) and/or a printer.

Computing device 104 also includes a processor 214 and a memory device 218. Processor 214 is coupled to user interface 204, presentation interface 207, and to memory device 218 via a system bus 220. In the exemplary embodiment, processor 214 communicates with the user, such as by prompting the user via presentation interface 207 and/or by receiving user inputs via user interface 204. The term "processor" refers generally to any programmable system including systems and microcontrollers, reduced instruction set circuits (RISC), application specific integrated circuits (ASIC), programmable logic circuits (PLC), and any other circuit or processor capable of executing the functions described herein. The above examples are exemplary only, and thus are not intended to limit in any way the definition and/or meaning of the term "processor."

In the exemplary embodiment, memory device 218 includes one or more devices that enable information, such as executable instructions and/or other data, to be stored and retrieved. Moreover, memory device 218 includes one or more computer readable media, such as, without limitation, dynamic random access memory (DRAM), static random access memory (SRAM), a solid state disk, and/or a hard disk. In the exemplary embodiment, memory device 218 stores, without limitation, application source code, application object code, configuration data, additional input events, application states, assertion statements, validation results, and/or any other type of data. Computing device 104, in the exemplary embodiment, may also include a communication interface 230 that is coupled to processor 214 via system bus 220. Moreover, communication interface 230 is communicatively coupled to sensing system 102 and to data management system 108 (shown in FIG. 16).

In the exemplary embodiment, processor 214 may be programmed by encoding an operation using one or more executable instructions and providing the executable instructions in memory device 218. In the exemplary embodiment, processor 214 is programmed to perform the techniques described herein.

During operation, as the subject is in a resting state, sensing system 102 detects a plurality of measurements of brain activity that is representative of at least one parameter of the brain of the subject. Sensing system 102 transmits at least one signal representative of the measurements to computing device 104 via data conduit 106. More specifically, the signals are transmitted to and received by communication interface 230 within computing device 104. Communication interface 230 then transmits the signals to processor 214 for processing and/or to memory device 218, wherein the data may be stored and transmitted to processor 214 at a later time. Processor 214 may generate an image of the plurality of measurements. Alternatively, sensing system 102 may transmit the signals to an imaging device (not shown), wherein an image of the measurements may be generated. The image may then be transmitted to computing device 104, wherein the image is stored within memory device 218 and transmitted to processor 214 for processing.

Moreover, data of other subjects may be transmitted to computing device 104 from database 110 (shown in FIG. 16) via network 109 (shown in FIG. 16). More specifically, the data may be received by communication interface 230 and then transmitted to processor 214 for processing and/or to memory device 218, wherein the data may be stored and transmitted to processor 214 at a later time. Computing device 104 may obtain the data at any time during operation.

In the exemplary embodiment, computing device 104 produces at least one map for each of the plurality of measurements received. Moreover, a user may see the image on the computing device 104, via presentation interface 207, and select the measurements, such as voxels, via user interface 204.

Figure 18:
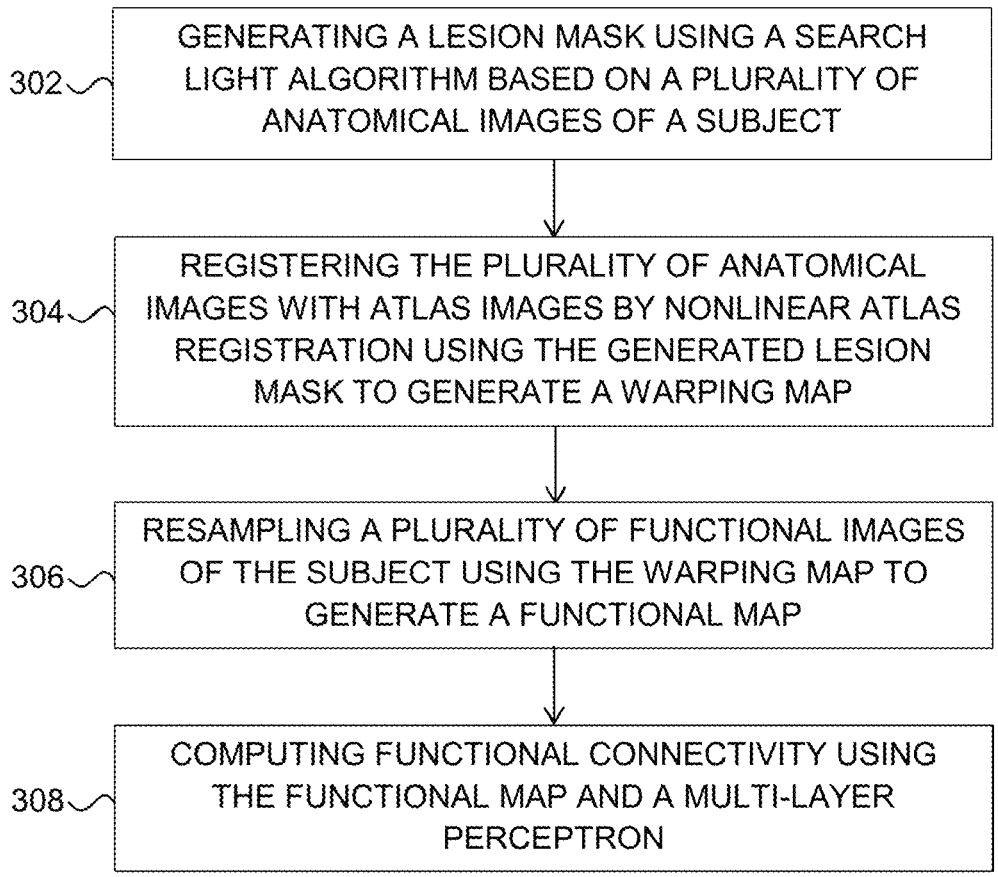
FIG. 18 is flow diagram of an exemplary method for task-less mapping of brain activity using the system shown in FIG. 16.

FIG. 18 is flow diagram of an exemplary method 300 for mapping brain function of a subject using system 100. At 302, a lesion mask is generated by the computing device 104 using a search light algorithm based on a plurality of anatomical images of the subject. The plurality of anatomical images are registered 304 with atlas images by nonlinear atlas registration using the generated lesion mask to generate a warping map. A plurality of functional images of the subject are resampled at 306 using the warping map to generate a functional map. Functional connectivity is then computed 308 using the functional map and a multi-layer perceptron.

The embodiments of the system and method for mapping of brain function of a subject, as described herein, were used in the following exemplary experiment. In example embodiments, the system 100 is configured to (e.g., the computing device 104 is programmed to) perform the techniques described below.

Reference dataset—For this experiment, the reference dataset comprised 100 individuals obtained from the Harvard-MGH Brain Genomics Superstruct Project. All participants were neurologically normal young adults (age 19-33 years) free of psychotropic medications. fMRI was acquired with a 3 Tesla Siemens Tim Trio scanner (repetition time (TR)=3.0 seconds, spatial resolution (3 mm)3 isotropic). Twelve minutes of resting state fMRI were acquired using a BOLD sensitized gradient echo (GRE) echo-planar imaging (EPI) sequence during which participants were instructed to fixate on a visual cross-hair, remain still, and not fall asleep. Anatomical imaging included one sagittal T1-weighted magnetization prepared rapid GRE (MP-RAGE) scan (T1w) and one T2-weighted scan (T2w).

Translational Imaging Protocol (TIP) dataset—The clinical data comprised 20 glioblastoma multiforme (GBM) patients aged 20-45 yrs (average 33.5 years), extracted from the Washington University School of Medicine (WUSM) neurosurgery brain tumor service database. Inclusion criteria were: new diagnosis of primary GBM; age above 18 years; clinical need for MRI at WUSM including fMRI for pre-surgical planning. Exclusion criteria were: prior brain surgery, inability to have an MRI scan. Analysis was conducted retrospectively after patients were already treated.

Patients were scanned with either a Siemens 3T Trio or Skyra scanner (Erlangen, Germany) using a standard clinical pre-surgical tumor protocol. Anatomical imaging included T1w magnetization prepared rapid acquisition GRE (MP-RAGE) and T2w fast spin echo, both with a voxel size of 1×1×1 mm. Resting state fMRI was acquired using a T2* EPI sequence (voxel size 3×3×3 mm; TE=27 ms; field of view=256 mm; flip angle=90°). Two runs in each patient were obtained; each run comprises of 160 frames with TR ranging from 2.2 s-2.67 s (mean: 2.38 s), SL algorithm—The SL algorithm localizes anatomically abnormal regions of the brain by evaluating voxel similarity (Fisher z-transformed Pearson spatial correlation) with respect to a standard template over a restricted spherical volume (the searchlight). In this work, the MNI152 nonlinear asymmetric atlas was used as the standard template. Scanning the searchlight over the whole brain generates a searchlight image (SLI). Preliminary experiments indicated that sampling the SL at a grid spacing equal to the SL radius is adequate. At each grid point, the voxel similarity value is assigned to all voxels within the SL. Thus, the finally obtained value is averaged over of several SL spheres.

Figure 1A:
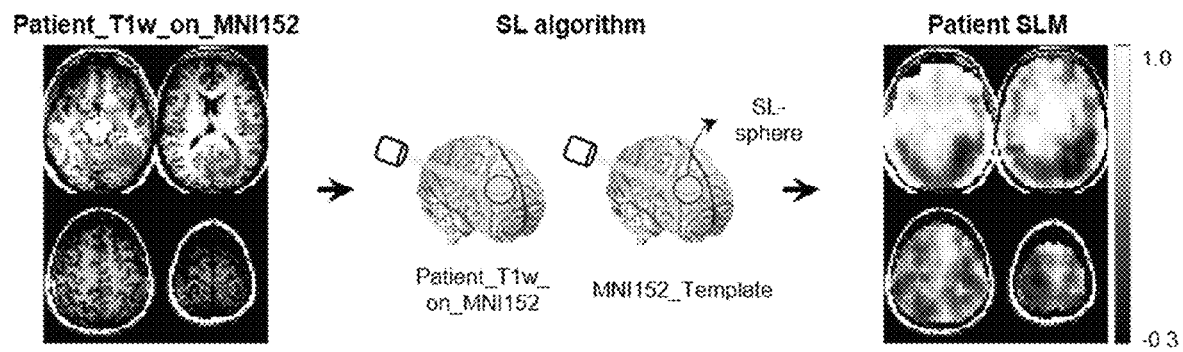
FIGS. 1A, 1B, and 1C are images illustrating an SL identification procedure.
Figure 1B:
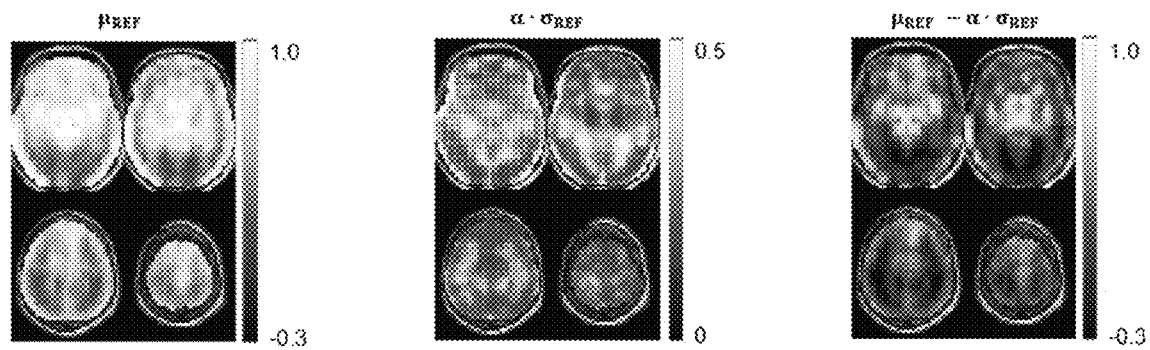
Figure 1C:
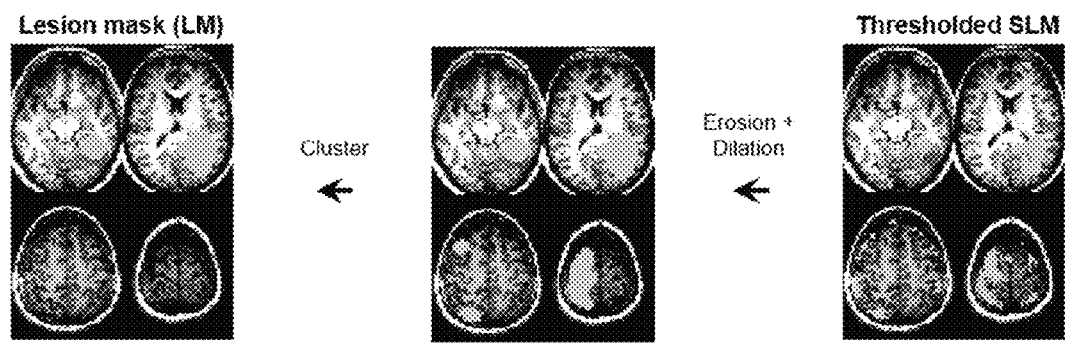

SL Lesion identification—The objective of computing SL images is to identify contiguous regions corresponding to lesions (FIG. 1A-1C). Accordingly, voxel-similarity maps must be thresholded. Additionally, it is necessary to take into account that normal anatomical structure leads to SLI non-uniformity. Thus, the threshold below which SLI values are considered abnormal is spatially dependent. To take into account this spatial dependence, the voxel-wise SLI mean ($\mu_{REF}$) and standard deviation ($\sigma_{REF}$) over the 100 reference subjects were evaluated. The [voxel-dependent] abnormality threshold then was defined as $$z_{thresh} = \mu_{REF} - \alpha \cdot \sigma_{REF}, \qquad (1)$$

where α is a patient-specific constant. The thresholding step generates a fragmented map (SLIt) in which the patient SLI is less than $z_{thresh}$. The SLIt must be additionally processed using a combination of erosion, dilation, and clustering operations to obtain the lesion mask (FIG. 1C). In greater detail, binary erosion is defined as $SLIt \ominus SE_r = \cap_{b \in SE_r} SLIt_{-b}$, where $SE_r$ is a spherical structuring element of radius r and $SLIt_{-b}$ denotes translation of SLIt by −b. Binary dilation is defined as $SLIt \oplus SE_r = \cup_{b \in SE_r} SLIt_b$, where $SLIt_b$ denotes translation of SLIt by b. Erosion and dilation generally are repeated. The lesion mask then is defined by clustering as the largest face-connected contiguous region. At the current state of algorithmic development, the values of parameters α, $SE_r$, and dilation/erosion/clustering sequence and repetition counts assume default values but are operator-adjustable. The operator adjusts these values via a GUI that displays the segmented lesion mask.

FIGS. 1A-1C, sometimes referred to collectively as FIG. 1, illustrate the SL lesion identification procedure. In FIG.

1A, the patient's T1w is initially registered to the atlas representative template without masking. A patient-specific SLI is generated by scanning the SL over the voxel-similarity image obtained by comparison of the patient's registered T1w to the template. In FIG. 1B, voxel-wise SLI mean ($\mu_{REF}$) and standard deviation ($\sigma_{REF}$) representing 100 reference subjects. An abnormality threshold map is computed according to Eq. 1. In FIG. 1C, in the right image comparison of the patient's SLI vs. the abnormality threshold map generates an initial binarized lesion mask. The middle image in FIG. 1C shows intermediate result following multiple erosion-dilation steps. The left image of FIG. 1C is a final lesion mask (LM) generated by retaining only the largest cluster.

SL radius selection—In principle, regions of low voxel similarity reveal anatomical abnormalities, e.g., tumor masses. A small SL sphere radius preserves spatial specificity but may lead to a noisy SL image; a large SL radius reduces noise but also reduces spatial specificity. To optimize the SL radius in the experiment, 700 SL images were generated using a 100 subject reference dataset and a range of radius options ($R_{SL}$(mm) $\in$ {6, 9, 12, 15, 18, 21, 24}). The optimal $R_{SL}$ for the experiment was determined by computing a reliability index as described below. This analysis determined that the optimal radius was $R_{SL}$=9 mm (3 voxels in 3 mm$^3$ atlas space).

Determination of optimal searchlight sphere radius—Instead of direct segmentation, the searchlight (SL) strategy localizes tumor masses by finding localized regions of abnormal anatomy relative to the standard template (here, the MIN152 atlas). Following initial registration of a given T1-weighted image to the template, local similarity is evaluated as the Pearson spatial correlation over a small spherical region (the SL). Systematically scanning the SL over the brain generates a SL image (SLI). A small SL radius preserves spatial specificity but may lead to a noisy SLI; a large SL radius reduces noise but also reduces spatial specificity.

To optimize the SL radius, SL images (relative to the standard template) were generated over the 100 subject reference dataset, systematically varying the SL radius over a range of options ($R_{SL}$ (mm) $\in$ {6, 9, 12, 15, 18, 21, 24}). The optimal SL radius was defined as that yielding the most consistent SLIs over the reference dataset taken pairwise. Thus, for each $R_{SL}$, a reliability index was computed, as $\mu_{sim}/\sigma_{sim}$, where $\mu_{sim}$ is mean similarity over the 100C2 SL image pairs and $\sigma_{sim}$ is the standard deviation (FIGS. 8A-8C—collectively FIG. 8). Diagonal blocks in FIG. 8A represent inter-subject SLI similarity at a fixed radius; off-diagonal blocks represent inter-subject SLI similarity at different radii. Within-block diagonal entries represent intra-subject similarity across radii. The mean ($\mu_{sim}$) and standard deviation ($\sigma_{sim}$) was evaluated over each block. FIG. 8B shows block-wise $\mu_{sim}$ and $\sigma_{sim}$ in the matrix upper and lower triangles. FIG. 8C shows $\mu_{sim}/\sigma_{sim}$ in each block. This analysis determined that the optimal radius (red outline) is $R_{SL}$=9 mm (3 voxels in (3 mm)$^3$ atlas space).

Figure 2:
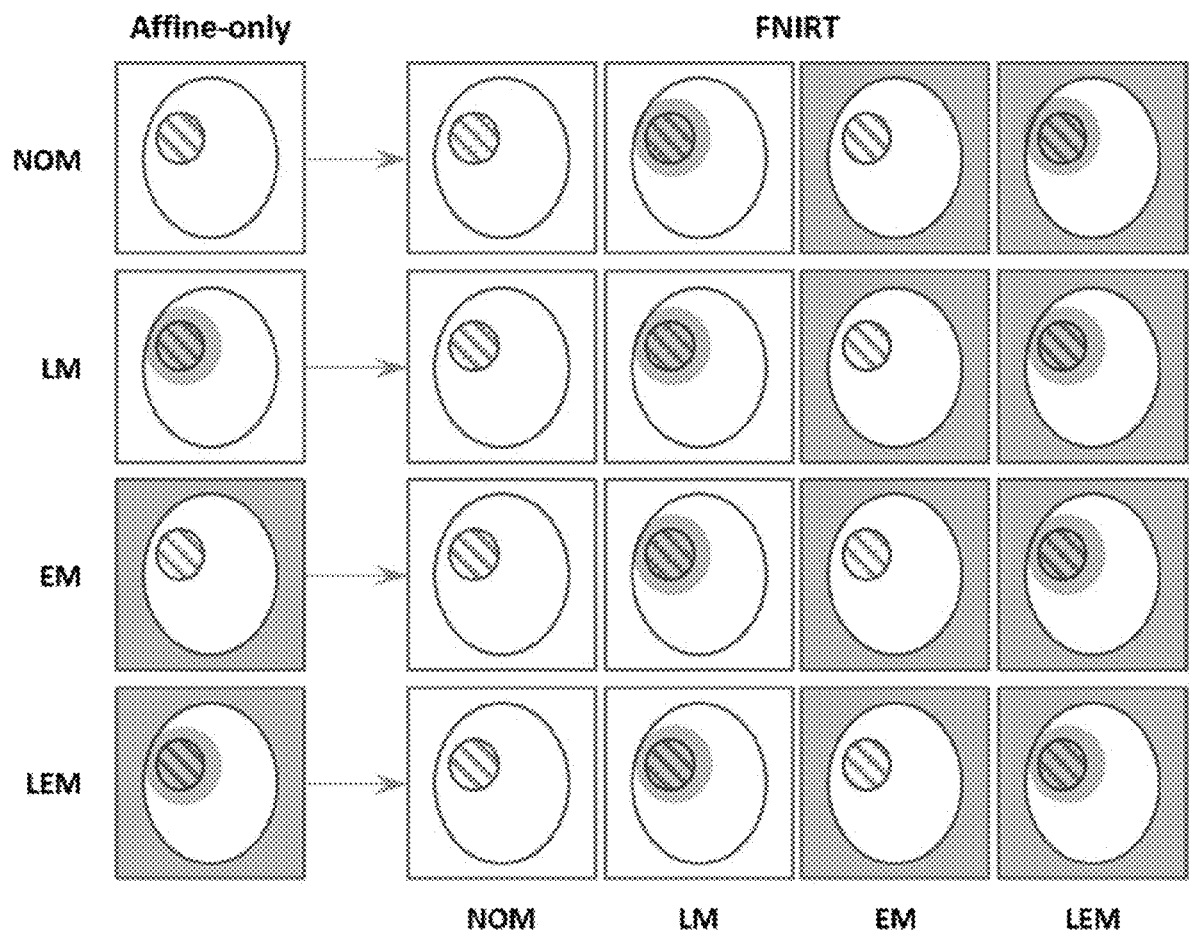
FIG. 2 is a schematic representation of T1w atlas registration options.
Figure 3:
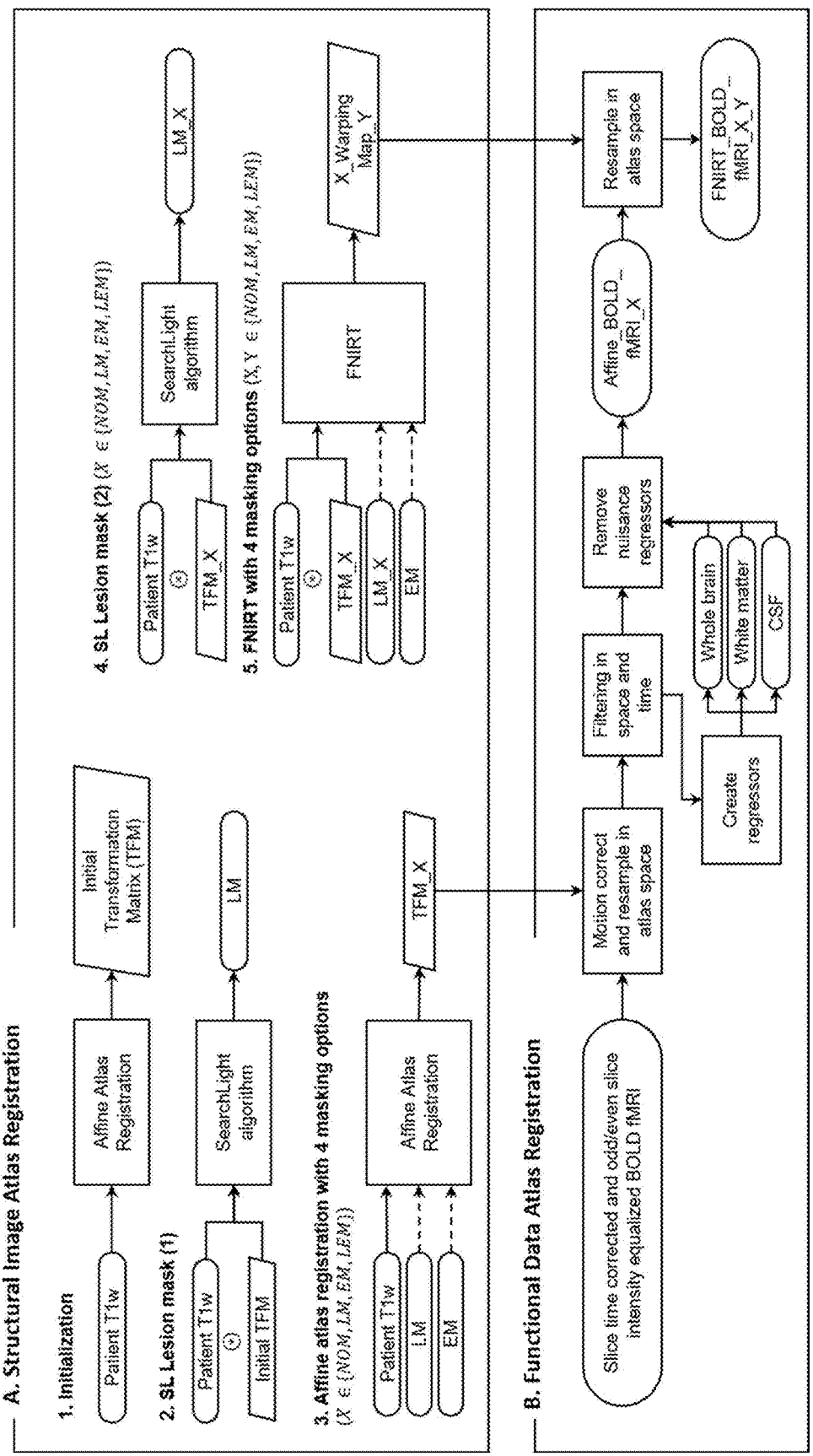
FIG. 3 is a block diagram of an example method of atlas registration according to embodiments of this disclosure.

Post lesion masking atlas registration—Several variant strategies for registering patient structural images to the atlas-representative template were studied. FIG. 2 is a schematic representation of T1w atlas registration options. FIG. 3 is a block diagram of an example method of atlas registration according to embodiments of this disclosure. In FIG. 3, box A includes the steps of structural image atlas registration, and box B includes the steps of functional data atlas registration. In FIG. 2, ellipses represent axial brain slices; hatched circular regions represent the structural abnormality.

Atlas registration was either affine-only or affine followed by nonlinear warping (FNIRT) (FIG. 3, Box A). Four masking options were tested: no mask (NOM), lesion mask (LM), extracranial tissue mask (EM), and combined LM+EM (LEM). Evaluation of the objective function was restricted to areas outside of the red shaded regions. All atlas registrations had been initialized by 12-parameter affine registration of the patient's T1w to the MNI152 template. The transformed image was input to SL algorithm and the resulting SL-lesion mask was used in subsequent atlas registration steps. Four masking options were tested: no mask (NOM), SL-lesion mask (LM), extracranial tissue mask (EM), and combined LM+EM (LEM) (FIG. 2, 1$^{st}$ column). The EM complement was defined in atlas space as voxels inside the brain plus a margin of ~2 mm. The objective function was conventional spatial correlation, evaluated as represented in FIG. 2. Thus, for example, in option LEM, objective function evaluation was restricted to areas within the brain but outside LM. Affine atlas registration, evaluated using each masking options, generated 4 images that were input to SL algorithm (FIG. 3, Box A, step 4). The resulting SL-lesion masks were used in subsequent non-linear registration steps (FIG. 3, Box A, step 5). Non-linear atlas registration (FNIRT) was run with the same 4 masking options, thereby generating 16 additional images (FIG. 2, columns 2-5). Finally, transformation matrices and warping maps, obtained from the affine and nonlinear atlas registration steps, were composed and the preprocessed fMRI data (described below) was resampled in register with the structural data in (3 mm)$^3$ atlas space (FIG. 3). Although FNIRT is described with respect to this example, other embodiments may use any other suitable nonlinear atlas registration, such as ANTS.

fMRI preprocessing—Initial fMRI preprocessing followed conventional practice. Briefly, this included compensation for slice-dependent time shifts, elimination of systematic odd-even slice intensity differences due to interleaved acquisition and rigid body correction of head movement within and across runs. The preprocessed fMRI data then were transformed using a composition of 4 transformation matrices and 16 warping maps connecting the fMRI volumes with the T1w structural image (FIG. 3).

For each atlas registration option, motion correction was included in a single resampling to generate volumetric timeseries in (3 mm)$^3$ atlas space. Additional preprocessing in preparation for functional connectivity analysis included spatial smoothing (6 mm full width at half maximum (FWHM) Gaussian blur in each direction), voxel-wise removal of linear trends over each fMRI run and temporal low-pass filtering retaining frequencies below 0.1 Hz. Spurious variance was reduced by regression of nuisance waveforms derived from head motion correction and timeseries extracted from regions in white matter and CSF. Nuisance regressors included the BOLD timeseries averaged over the brain, i.e., global signal regression (GSR) (FIG. 3).

Frame censoring was implemented using DVARS (D referring to temporal derivative of time courses, VARS referring to RMS variance over voxels), which indexes the rate of change of BOLD signal across the entire brain at each frame of data. The DVARS value corresponding to absent apparent head motion exhibits subject-to-subject variability that may reflect fluctuating arterial pCO2. DVARS cut-off of 0.45% was used for frame-censoring. Of total 320 frames, patients on average had 312.85±7.26 usable BOLD frames (294-318 frames).

With reference again to FIG. 3, Box A illustrates structural image atlas registration. FIG. 3, Box A, 1—Initialization:

Each patient's T1w is initially registered to the atlas representative template without masking. Initial affine transformation matrix (TFM) is obtained. FIG. 3, Box A, 2—First SL Lesion mask: Initial TFM maps Patient T1w to atlas representative template space. The transformed image is input to the SL algorithm, which outputs a lesion mask (LM). FIG. 3, Box A, 3—Affine atlas registration with 4 masking options: The patient's T1w is affine registered to the atlas representative template with 4 masking options. Four TFMs are obtained. FIG. 3, Box A, 4—Second SL Lesion mask: TFM_X maps the Patient T1w to template space. The transformed image is input to the SL algorithm, which outputs a lesion mask (LM_X). FIG. 3, Box A, 5—FNIRT with 4 masking options: The affine transformed image is registered to the atlas representative template using FNIRT with 4 masking options. A total of 16 warping maps are obtained. FIG. 3, Box B illustrates functional data atlas registration. Preprocessed BOLD fMRI data are resampled in atlas space using TFM_X. The data are filtered in space (6 mm FWHM Gaussian blur in each direction) and time (low-pass filter retaining frequencies below 0.1 Hz). Denoising is effected by regression of nuisance waveforms derived from white matter, CSF, and the signal averaged over the whole brain (GSR). The denoised volumetric time series (Affine_BOLD_fMRI_X) then are resampled in alas space (FNIRT) using X_WarpingMap_Y to generate FNIRT_BOLD_fMRI_X_Y. Symbol key: Rounded corner: image; Rectangle: procedure; Rhombus: transformation matrix/warping map.

Functional Connectivity (FC) and resting state network mapping using the Multi-layer Perceptron (MLP)-FC was computed on the basis of the preprocessed data in atlas space (affine or non-linearly registered) resampled to (3 mm)3 voxels. In greater detail, FC was evaluated as the Fisher z-transformed Pearson temporal correlation for all voxel pairs. The voxel×voxel FC matrix was input to a trained MLP classifier. The MLP assigns, to each voxel in the brain, membership values (range [0, 1]) for each of 7 RSNs+a noise category (Table 1). Additionally, FC was computed as a 169×169 matrix using the BOLD fMRI time series extracted from the 169 regions of interest (ROIs) used to train the MLP (Table 1). This choice of ROIs confers consistency across the present conventional FC and MLP-based FC evaluations.

TABLE 1

Resting State Networks (RSNs) and a number of seed ROIs corresponding to each RSN.

| RSN | Expanded acronym | Final seed ROIs |
|-----|------------------|-----------------|
| DAN | Dorsal attention network | 28 |
| VAN | Ventral attention network | 15 |
| SMN | Sensori-motor network | 39 |
| VIS | Visual network | 30 |
| FPC | Fronto-parietal control network | 12 |
| LAN | Language network | 13 |
| DMN | Default mode network | 32 |

Atlas registration Performance Quantitation—Quality of atlas registration was assessed both in terms of matching individual T1w images to the atlas representative template (described below) as well as measures derived from co-registered BOLD fMRI functional connectivity (described below). A total of 20 registration options (FIG. 3) was compared. Since the patient dataset was markedly heterogeneous with respect to tumor size, the 20 atlas registration options were compared using the Friedman non-parametric test, which measures consistency of registration option rank across patients and returns a test statistic that is distributed approximately as chi-squared. The Nemenyi post-hoc test was used to assess the significance of differences between the 20 options taken pairwise. The performance of two registration options was considered significantly different if the corresponding average ranks differed by at least the critical difference (CD):

$$CD = q_\alpha \sqrt{k(k+1)/6N} = 6.21 \qquad (2)$$

where critical values, $q_\alpha$, are based on the studentized range statistic divided by $\sqrt{2}$. Here, as we are comparing 20 options, $q_\alpha$=3.319.

Figure 9:
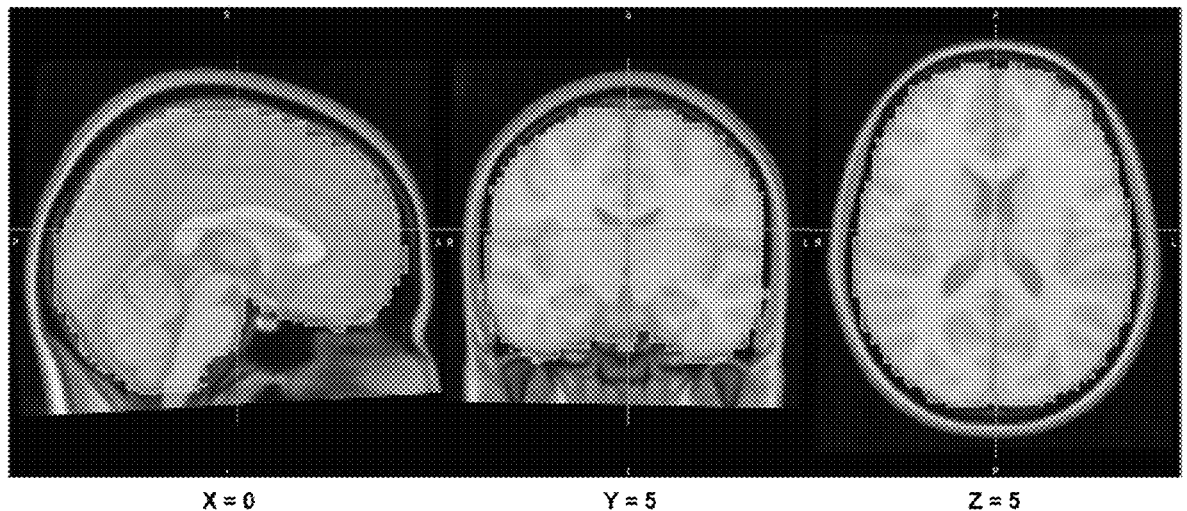
FIG. 9 shows the use of the intracranial mask to evaluate the quality of registration of each patient's structural image to the MNI152 template.

Evaluation of Structural Normalization—Quality of structural normalization was assessed as the Pearson spatial correlation, evaluated over the brain (FIG. 9), of each subject's atlas-transformed T1w with the MNI152 template. Lesions were not masked in this evaluation. FIG. 9 shows the use of the intracranial mask to evaluate the quality of registration of each patient's structural image to the MNI152 template. The mask was defined in atlas space as the complement of the extracranial mask (EM) plus a margin of ~2 mm.

Evaluation of Functional Connectivity—Quality of FC was assessed as the similarity of each patient's 169×169 FC matrix to the same measure averaged over the reference dataset (FIG. 5A). In greater detail, similarity was computed as Pearson correlation of the vectorized [upper triangle] FC matrix. Thus, the dimensionality of the vector was C(169, 2)=14,196. FC quality was additionally evaluated in terms of the root mean square error (RMSE) measure of MLP performance, which quantitates the goodness of fit of voxel-wise RSN membership estimation. The FC similarity measure and the MLP-derived RMSE are related as the present reference dataset contributed to training the MLP.

Figure 4A:
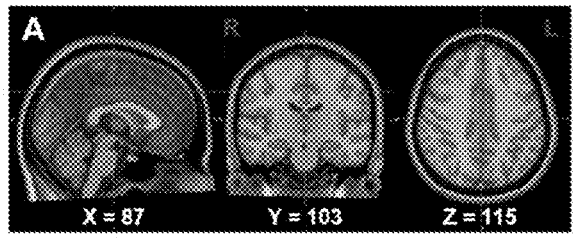
FIGS. 4A, 4B, 4C, 4D, 4E, and 4F illustrate structural normalization results obtained with and without non-linear warping (FNIRT).
Figure 4B:
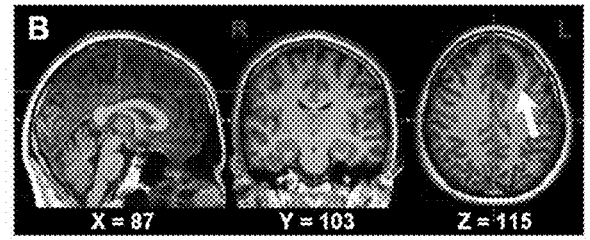
Figure 4C:
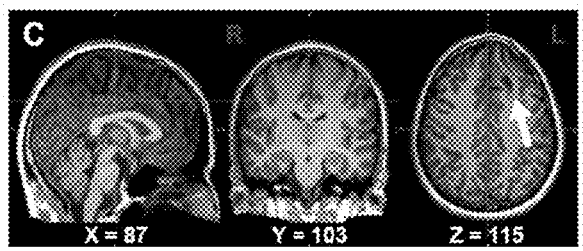
Figure 4D:
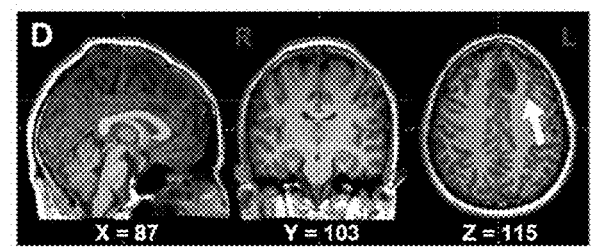
Figure 4E:
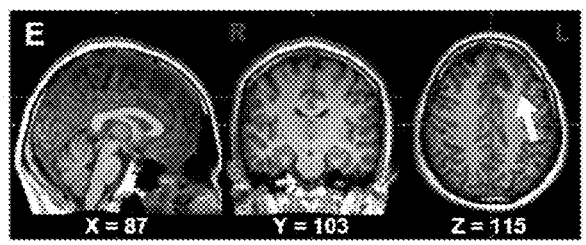
Figure 4F:
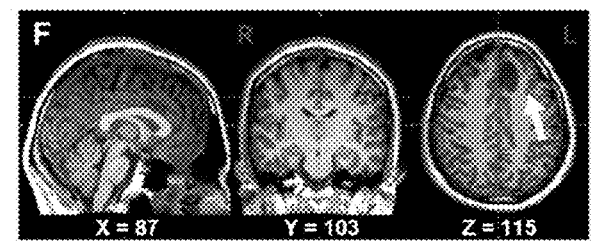

Structural normalization—FIGS. 4A-4F (collectively FIG. 4) illustrate structural normalization results obtained with and without non-linear warping (FNIRT). FIG. 4A shows the MNI152 template. FIG. 4B shows a structural image obtained using affine registration with LEM masking (X=LEM in FIG. 3, Box A). The structural image shown in FIG. 4B was used in subsequent non-linear registration steps. FIGS. 4C-4F illustrate results obtained with 4 different FNIRT masking options in a representative patient. FIG. 4C: FNIRT without masking (Y=NOM in FIG. 3A). FIG. 4D: FNIRT with LM (Y=LM in FIG. 3A). FIG. 4E: FNIRT with EM (Y=EM in FIG. 3A). FIG. 4F: FNIRT with LEM (Y=LEM in FIG. 3A).

Differences dependent on masking options are most evident around the lesion. The affine result (FIG. 4B) preserves tumor proportions relative to the rest of the brain. FNIRT without masking (FIG. 4C) shrinks the lesion, distorts nearby regions, and blurs the tumor boundary. Marked warping is reflected in the curvature of the originally acquired most inferior slice (evident on the sagittal and coronal views). Masking out the tumor during FNIRT (FIG. 4D) preserves the relative proportions of the tumor, as in the affine result, while warping the rest of the brain to more closely match the template.

fMRI results—FIGS. 5A-5F (collectively FIG. 5) illustrate functional connectivity matrices averaged over the 20 patients. FIG. 5A shows results obtained with the reference dataset. FIG. 5B shows results obtained with affine atlas registration (X=LEM in FIG. 4). FIGS. 5C-5F illustrate results obtained with FNIRT and 4 different Y masking options (see FIG. 4). FIG. 5C: X=LEM, Y=NOM. FIG. 5D: X=LEM, Y=LM. FIG. 5E: X=LEM, Y=EM. FIG. 5F: X=LEM, Y=LEM. FC similarity values are shown below each matrix. The patients showed generally weaker FC in comparison to the reference cohort. Thus, positive correlations (warm hues) were less positive and negative correlations (cold hues) were less negative. The effects of various atlas registration options (affine vs. FNIRT, masking) were relatively subtle and not easily discerned by inspection of the matrices. The greatest objective similarity to the reference dataset was obtained with FNIRT+LEM (r=0.8740; panel F).

Figure 6A:
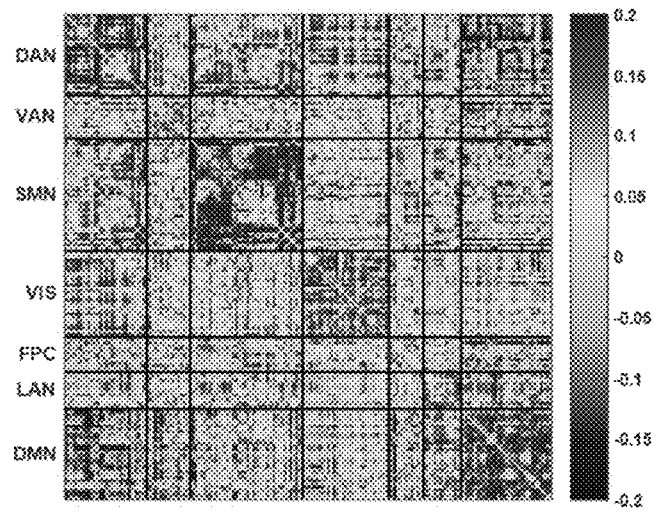
FIG. 6A is a difference matrix obtained by subtracting the patient average FC matrix (FIG. 5F) from the reference dataset average FC matrix (FIG. 5A).
Figure 6B:
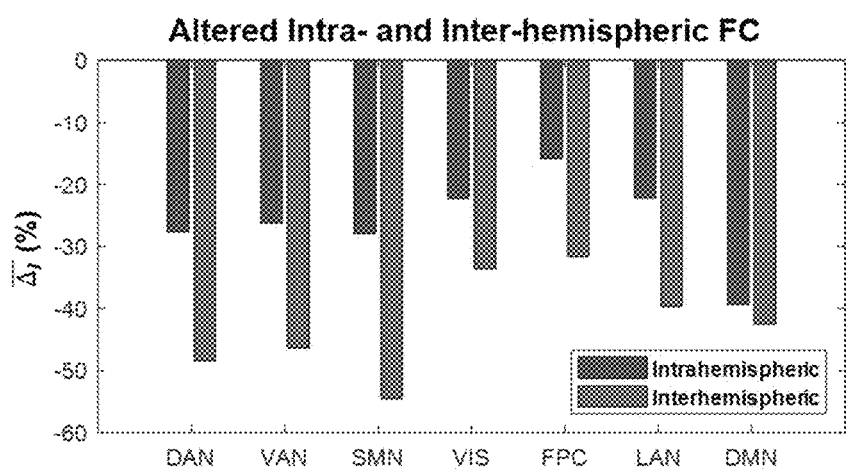
FIG. 6B is a graph of Group difference in intra- vs. inter-hemispheric FC within RSN.
Figures 7A, 7C:
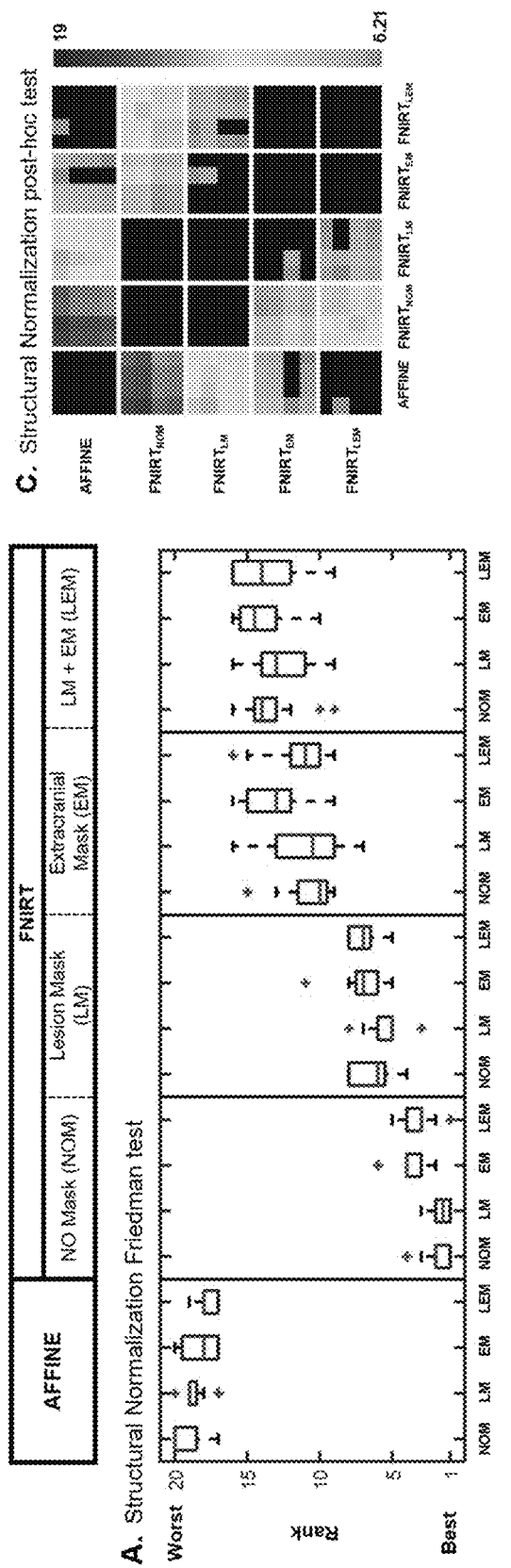
FIGS. 7A, 7B, 7C, and 7D plot Friedman rank sum and Nemenyi post-hoc test results for both structural and functional quality measures.
Figures 7B, 7D:
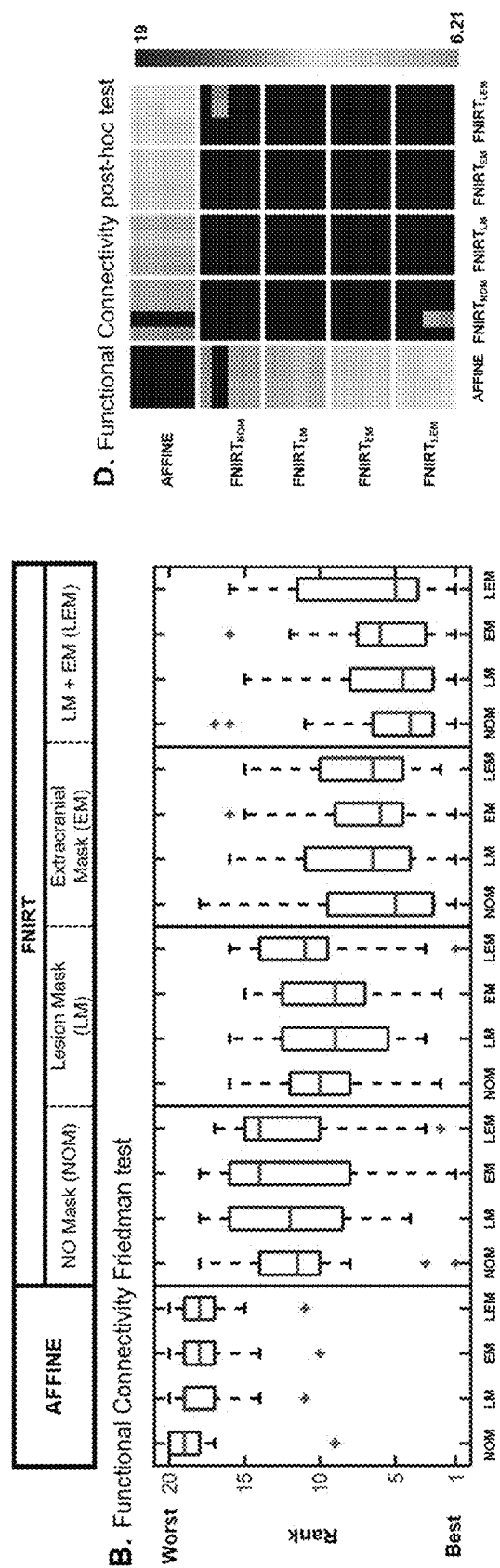

To study consistent differences between the patient vs. the reference datasets, the FNIRT+LEM matrix was subtracted from the reference matrix (FIG. 5A-FIG. 5F). This result is shown in FIGS. 6A and 6B (collectively FIG. 6). Negative as well as positive correlations were generally weaker in magnitude in the patients. Thus the difference matrix shown in FIG. 6 recapitulates the major features in the un-differenced matrices shown in FIG. 5. However, this matrix also showed within-block structure, which raised the question of whether brain tumors systematically induce focal changes in FC. Several alternative hypotheses (e.g., dependence on ROI-ROI geometric distance or vector orientation) were examined but proved to be unrevealing. However investigation of within RSN, i.e., within each of the difference matrix diagonal blocks, revealed that inter-hemispheric FC was more reduced as compared to intra-hemispheric FC. This finding was obtained in all RSNs except the DMN (FIG. 6B). FIG. 6B graphs group difference in intra- vs. inter-hemispheric FC within RSN. This analysis considers only correlations within diagonal blocks. Each entry corresponds to an ROI pair that is either intra- or inter-hemispheric. The bars represent the mean patient—reference FC difference expressed as percent change. Thus, $\overline{\Delta}_I$ (%)=100· $(FC_{I,pat}-FC_{I,ref})/FC_{I,ref}$ where I represents intra- or inter-hemispheric FC in the patients (pat) or reference data (ref), and over-bars represent averages over group. $\overline{\Delta}_I$ is evaluated separately for each RSN Statistical evaluation of results obtained with different atlas registration options—An objective is to improve atlas registration of resting state fMRI in the context of FC mapping. The entire procedure entails, first, matching each patient's structural image to an atlas-representative template and, second, RSN mapping on the basis of the resting state fMRI data. Thus, quality of the structural and functional components were evaluated separately. FIGS. 7A-7D (collectively FIG. 7) illustrate the effects of various atlas registration options on both structural normalization and FC mapping. Box plots in FIGS. 7A (Structural normalization) and 7B (Functional connectivity similarity to reference dataset) represent ranks scores corresponding to each of 20 atlas registration options (FIG. 2). Lower rank corresponds to better quality. The matrices in FIGS. 7C and 7D represent Nemenyi test results comparing all atlas registration options. Nemenyi scores <6.21 are not significant and are represented as dark blue. Relatively homogeneous blocks indicate little impact of masking option at the affine stage. In contrast, masking option during FNIRT yielded significant effects represented as non-dark blue blocks. A non-parametric approach to statistical evaluation (rank-order comparison using the Friedman test) was used in view of substantial inter-subject heterogeneity and quantitatively small effect sizes. There was a significant effect of atlas registration option (structural: Q=354.2, p<10-6; functional: Q=204.8, p<10-6). A principal finding evident in FIG. 7 is that FNIRT improved both the structural and functional results. Masking option at the affine stage (option X in FIG. 3) negligibly impacted the final results. This outcome is represented in FIG. 7C, D as the absence of significance in all (uniformly dark blue) diagonal blocks and relatively homogeneous off-diagonal blocks. Masking option during the FNIRT stage (option Y in FIG. 3) significantly impacted the final results. Importantly, the direction of these effects was opposite in the structural vs. functional analyses (upward vs. downward trends in FIG. 7A vs. FIG. 7B). Thus, the best structural normalization was obtained with no masking whereas the best FC match to the reference dataset was obtained with lesion+extracranial tissue masking.

Figure 10:
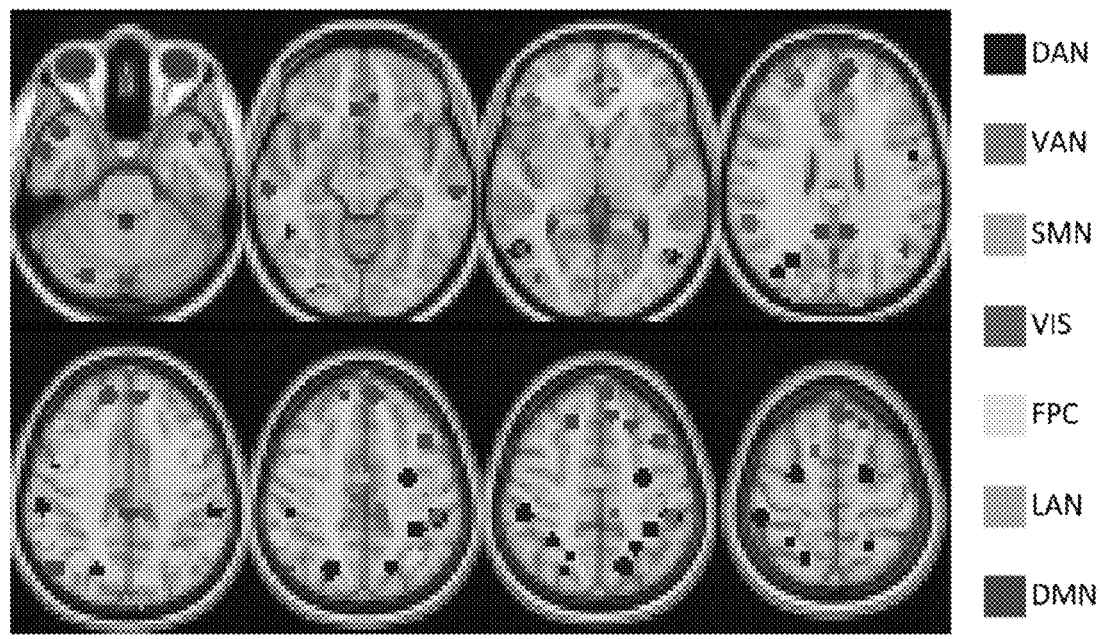
FIG. 10 shows the Seed ROIs used to generate correlation matrices.
Figures 11A, 11B:
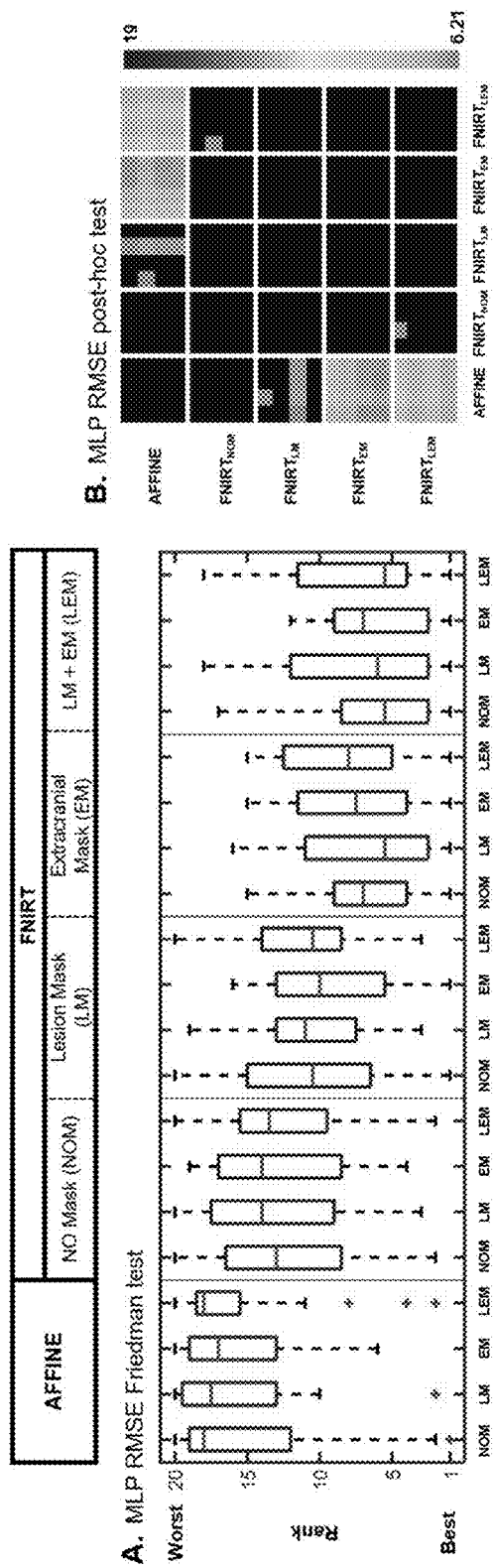
FIGS. 11A and 11B plot Friedman rank sum and Nemenyi post-hoc test results for FC quality evaluated in terms of MLP classification error.

Quality of FC mapping was additionally evaluated using MLP classification error. This error is 0 if RSN membership at a given voxel is completely certain and greater than 0 in proportion to RSN membership uncertainty. The effect of atlas registration option was evaluated by ranking classification error averaged over all voxels within seed ROIs. FIG. 10 shows the Seed ROIs used to generate correlation matrices. RSN designations and color code match. ROI counts in each RSN are listed in Table 1. The classification error results were similar to those obtained in terms of FC matrix similarity. FIGS. 11A and 11B plot Friedman rank sum and Nemenyi post-hoc test results for FC quality evaluated in terms of MLP classification error. The Box plot in FIG. 11A represent rank scores corresponding to each of 20 atlas registration options (FIG. 2). Lower rank corresponds to better quality. The matrix in FIG. 11B represents Nemenyi test result comparing all atlas registration options. Nemenyi scores <6.21 are not significant and are represented as dark blue. Relatively homogeneous blocks indicate little impact of masking option at the affine stage. In contrast, masking option during FNIRT yielded significant effects represented as non-dark blue blocks. As in FIG. 7B, there was a significant effect of atlas registration option (Q=118.9, $p<10^{-6}$) and an improvement in FC quality with FNIRT. As observed with FC quality evaluated in terms of matrix similarity, the best results were obtained with option LEM at the FNIRT stage. The Nemenyi post-hoc test results are similar to those shown in FIG. 7D but quantitatively less significant.

Figures 12A, 12C:
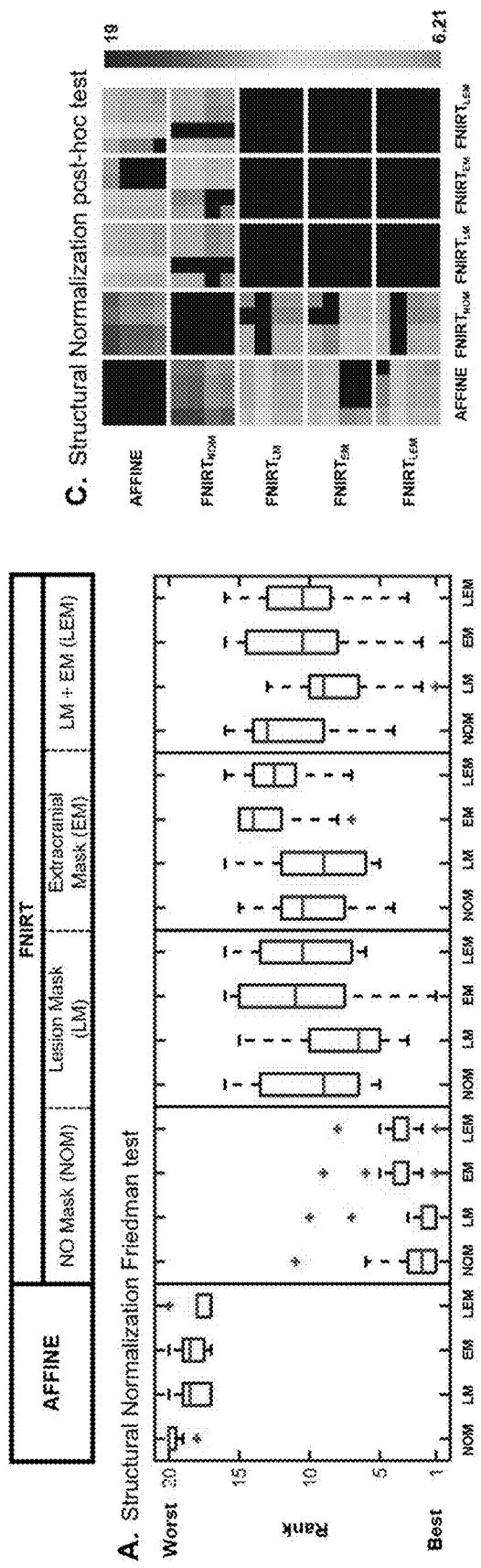
FIGS. 12A, 12B, 12C, and 12D plot Friedman rank sum and Nemenyi post-hoc test results for both structural and functional quality measures (excluding lesion mask).
Figures 12B, 12D:
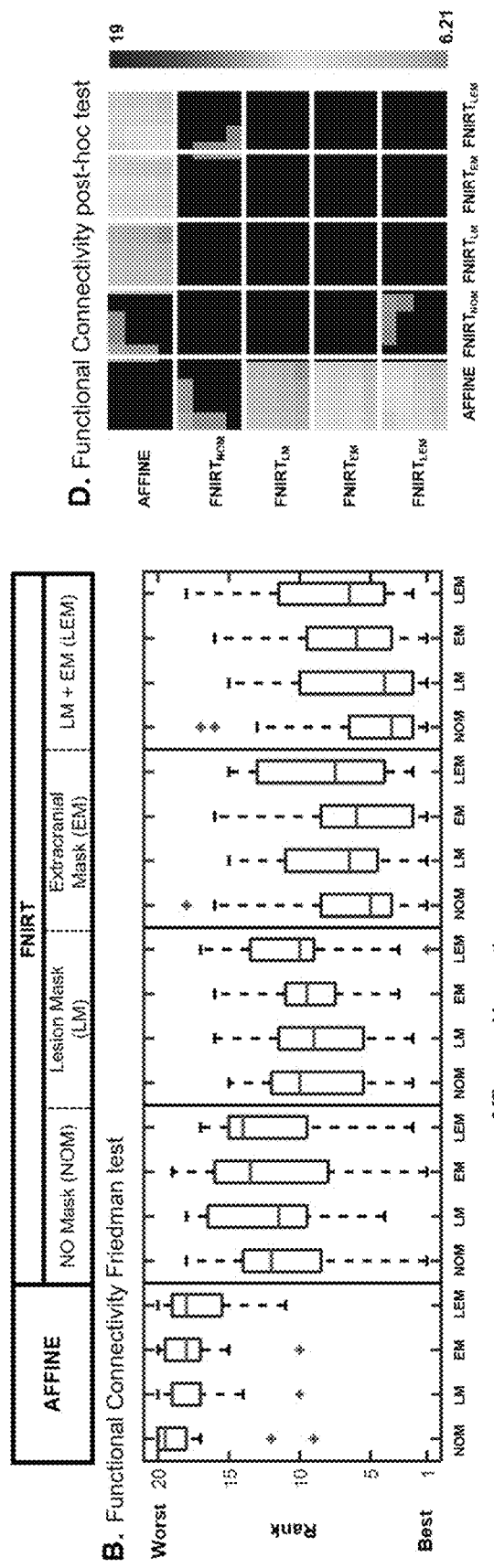

To investigate the effect of lesion in both structural and functional results, rank-order comparisons on outcome measures (structural normalization and FC similarity to reference dataset) excluding the lesion area were evaluated. These results are shown in FIGS. 12A-12D (collectively FIG. 12). The structural normalization results were somewhat more variable but otherwise the results shown in FIGS. 7 and 12 are comparable. Friedman rank sum and Nemenyi post-hoc test results for both structural and functional quality measures (exclude lesion mask). As observed in FIG. 7A, the best structural normalization was obtained with no masking. However, as shown in FIG. 12C, the quality of subject's atlas-transformed T1w generated using other masking options was comparable. As observed in FIG. 7B, the best results were obtained with option LEM at the FNIRT stage. The Nemenyi post-hoc test results are similar to those shown in main text FIG. 7D but quantitatively less significant.

Figure 13:
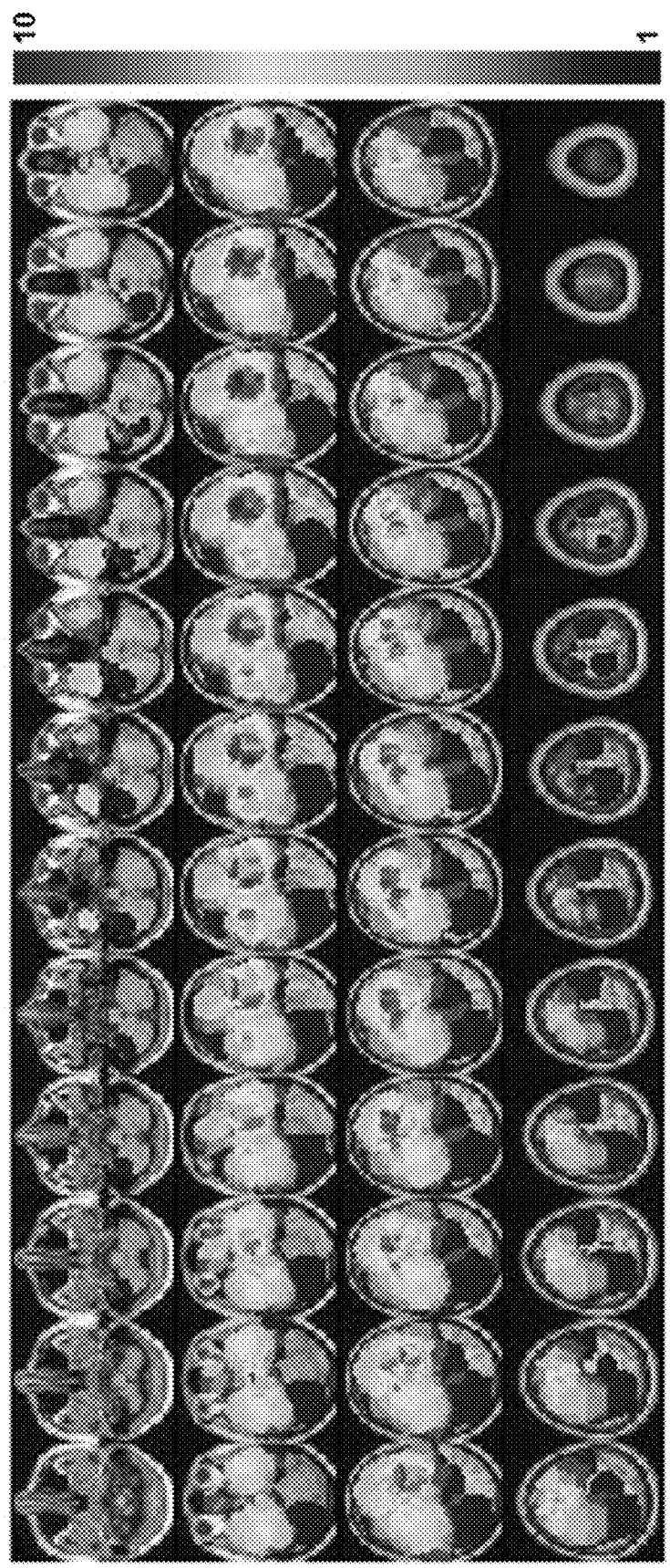
FIG. 13 is a tumor frequency map.
Figure 15B:
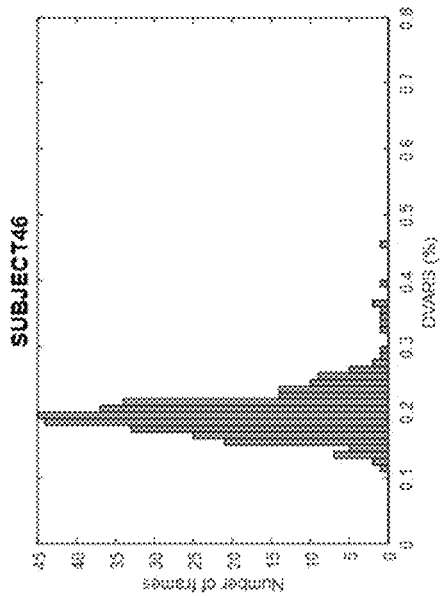
FIGS. 15A, 15B, 15C, and 15D are graphs of DVARS measure evaluated in patients with low movement (FIGS. 15A and 15B) and high movement (FIGS. 15C and 15D).
Figure 15D:
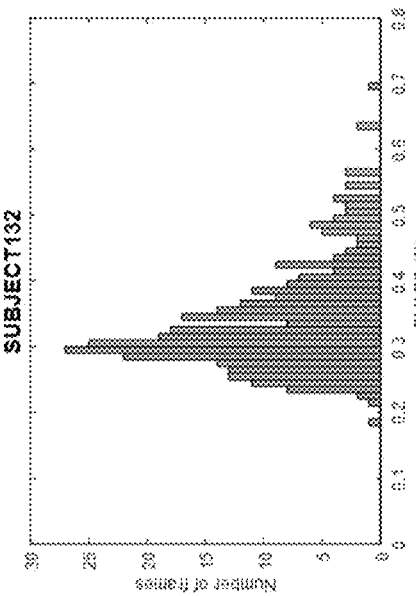
Figure 15A:
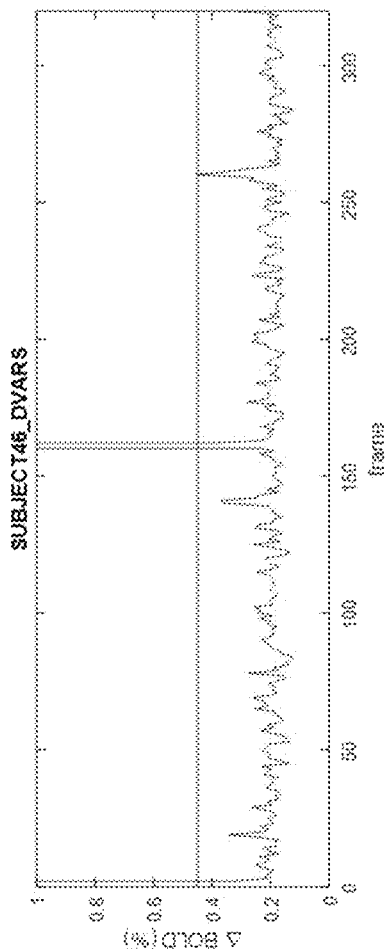
Figure 15C:
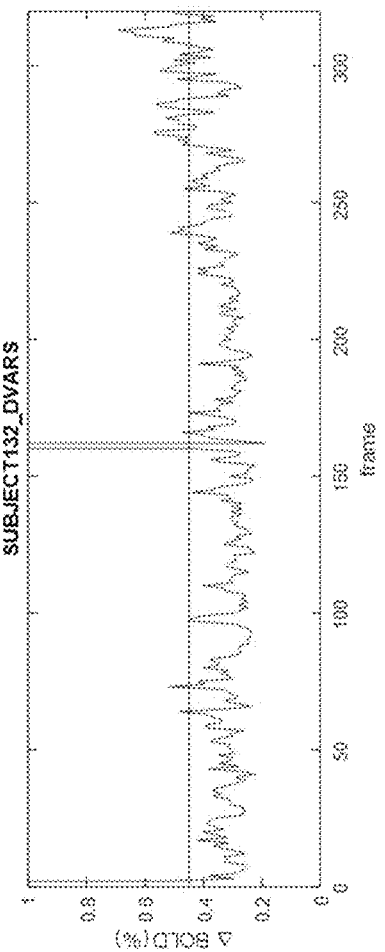

FIG. 13 is a tumor frequency map. FIGS. 14A-14D (collectively FIG. 14) are graphs of representative translation and rotation realignment parameters calculated in patients with low movement (FIGS. 14A and 14B) and high movement (FIGS. 14C and 14D). The same two patients are represented in FIG. 15. FIGS. 15A-15D are graphs of DVARS (D referring to temporal derivative of timecourses, VARS referring to RMS variance over voxels) measure evaluated in patients with low movement (FIGS. 15A and 15B) and high movement (FIGS. 15C and 15D). The same two patients are represented in FIG. 14.

An objective of this investigation is to improve atlas registration of resting state functional MRI (rs-fMRI) in the context of pre-surgical mapping of function in patients with brain tumors. To this end, we investigated affine vs. non-linear (FNIRT) atlas registration and several associated masking options. We assessed both quality of spatial normalization (match to atlas representative template) and quality of resting state network (RSN) mapping (match to reference FC data). Reliable resting state network (RSN) mapping depends on precise spatial normalization. However, it is possible that the optimal atlas registration strategy may differ depending on which outcome measure is assessed. Indeed, this was the observed result: FNIRT (in comparison to affine warping) improved both the structural and functional results, but different masking options optimized the structural vs. functional results. Thus, whereas the best structural normalization was obtained with no masking, the best RSN mapping was achieved with lesion+extracranial tissue masking. This result is understandable as FNIRT optimizes the match to template by shrinking the lesion. A necessary correlate is expansion and deformation of the surrounding tissue. This effect is illustrated in FIG. 4C. This distortion propagates to the functional data and compromises RSN mapping.

Structural normalization is a non-trivial challenge in patients with brain tumors. In the presence of distorted anatomy, non-linear atlas registration attempts to reduce image mismatch, which leads to distortion of extra-lesional brain and inaccurate functional localization. Cost-function masking (CFM) has been suggested as a means of improving spatial normalization in patients with brain tumors. Although the value of CFM is not in question, the precision of the lesion mask potentially affects the quality of structural normalization. However, it has been shown that the precision of the mask is not a key factor in the success of CFM. Accordingly, we developed the searchlight algorithm to create a generous lesion mask, obviating the need for direct lesion segmentation.

To explore the influence of skull-stripping on the registration process, we evaluated extracranial tissue masking (EM) as one of the options. Results determined that extracranial tissue masking improves the quality of RSN mapping. This result is consistent with a previous study showing that skull stripping improved language localization.

Abnormal functional connectivity in brain tumor patients potentially is attributable to several pathophysiological causes. These include destruction of normally functioning parenchyma and white matter, increased intracranial pressure due to mass effect or edema, impaired neurovascular coupling, and vasomotion. Imprecise spatial normalization would be a procedural cause of factitiously abnormal functional connectivity that we here sought to minimize.

Systematic FC differences were observed between tumor patients and controls that deserve comment. Our set of seed ROIs used to explore this question is considerably broader than that used in prior work. On comparison of the group average FC matrix of the reference dataset to the patient dataset, we observed that FC topography in tumor patients is remarkably normal although generally somewhat weaker in magnitude. This finding is broadly consistent with prior reports. Furthermore, we observed a greater inter-hemispheric FC loss in tumor patients, as has been previously reported. In our data, loss of DMN FC was equally present intra- as well as inter-hemispherically. This result may simply reflect the effect of location of the DMN seed ROIs, which are closer to the midline.

Exemplary embodiments of the system, apparatus, and method are described above in detail. The system, apparatus, and method are not limited to the specific embodiments described herein, but rather, components of the system and apparatus, and/or steps of the methods may be utilized independently and separately from other components and/or steps described herein. For example, but not limited to, the system may also be used in combination with other apparatus, systems, and methods, and is not limited to practice with only the system as described herein. Rather, the exemplary embodiment can be implemented and utilized in connection with many other applications.

Although specific features of various embodiments of the invention may be shown in some drawings and not in others, this is for convenience only. In accordance with the principles of the invention, any feature of a drawing may be referenced and/or claimed in combination with any feature of any other drawing.

Although described in connection with an exemplary computing system environment, embodiments of the invention are operational with numerous other general purpose or special purpose computing system environments or configurations. The computing system environment is not intended to suggest any limitation as to the scope of use or functionality of any aspect of the invention.

Embodiments of the invention may be described in the general context of computer-executable instructions, such as program modules, executed by one or more computers or other devices. The computer-executable instructions may be organized into one or more computer-executable components or modules. Generally, program modules include, but are not limited to, routines, programs, objects, components, and data structures that perform particular tasks or implement particular abstract data types. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein. Aspects of the invention may also be practiced in distributed computing environments where tasks are performed by remote processing devices that are linked through a communications network. In a distributed computing environment, program modules may be located in both local and remote computer storage media including memory storage devices.

In operation, a computer executes computer-executable instructions embodied in one or more computer-executable components stored on one or more computer-readable media to implement aspects of the invention described and/or illustrated herein.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In some embodiments, numbers expressing quantities of ingredients, measurements, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples. As various changes could be made in the above constructions and methods without departing from the scope of the disclosure, it is intended that all matter contained in the above description and shown in the accompanying drawing(s) shall be interpreted as illustrative and not in a limiting sense.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for mapping brain function of a subject, the method comprising:
   receiving a plurality of functional images of a brain of the subject ascertained during a resting state;
   receiving a plurality of anatomical images of the brain of the subject;
   defining one or more regions in the plurality of anatomical images to be excluded from atlas registration of the plurality of anatomical images;
   registering the plurality of anatomical images with atlas images by nonlinear atlas registration with the defined one or more regions excluded to generate a warping map;
   registering the plurality of functional images with atlas images using the warping map to guide the registration; and
   computing functional connectivity of the brain of the subject using the registered functional images.

2. The method of claim 1, further generating a resting state network map of the brain of the subject based on the computed functional connectivity of the brain of the subject.

3. The method of claim 2, wherein generating a resting state network map of the brain of the subject comprises inputting the computed functional connectivity into a neural network trained to estimate class membership for voxels of functional images of the brain to a plurality of resting state networks.

4. The method of claim 3, wherein the neural network comprises a multilayer perceptron.

5. The method of claim 1, wherein the plurality of functional images of a brain of the subject comprises resting state functional magnetic resonance imaging (rs-fMRI) images.

6. The method of claim 1, wherein defining one or more regions to be excluded from atlas registration comprises executing a searchlight algorithm programmed to compare voxels of the plurality of anatomical images to corresponding voxels of a plurality of atlas images.

7. The method of claim 6, wherein the searchlight algorithm is programmed to identify one or more lesions of the brain of the subject based on the comparison of voxels of the plurality of anatomical images to corresponding voxels of the plurality of atlas images and to use the identified lesions as the one or more regions in the plurality of anatomical images to be excluded from atlas registration of the plurality of anatomical images.

8. A computing device for use in a system for mapping brain function of a subject, the computing device comprising:
   a processor; and
   a memory storing instructions that, when executed by the processor, cause the processor to:
   receive a plurality of functional images of a brain of the subject ascertained during a resting state;

receive a plurality of anatomical images of the brain of the subject;

define one or more regions in the plurality of anatomical images to be excluded from atlas registration of the plurality of anatomical images;

register the plurality of anatomical images with atlas images by nonlinear atlas registration with the defined one or more regions excluded to generate a warping map;

register the plurality of functional images with atlas images using the warping map to guide the registration; and compute functional connectivity of the brain of the subject using the registered functional images.

9. The computing device of claim 8, wherein the memory includes instructions that cause the processor to generate a resting state network map of the brain of the subject based on the computed functional connectivity of the brain of the subject.

10. The computing device of claim 9, wherein the memory includes instructions that cause the processor to generate the resting state network map of the brain of the subject by inputting the computed functional connectivity into a neural network trained to estimate class membership for voxels of functional images of the brain to a plurality of resting state networks.

11. The computing device of claim 10, wherein the neural network comprises a multilayer perceptron.

12. The computing device of claim 8, wherein the plurality of functional images of a brain of the subject comprises resting state functional magnetic resonance imaging (rs-fMRI) images.

13. The computing device of claim 8, wherein the memory includes instructions that cause the processor to define one or more regions to be excluded from atlas registration by executing a searchlight algorithm programmed to compare voxels of the plurality of anatomical images to corresponding voxels of a plurality of atlas images.

14. The computing device of claim 13, wherein the searchlight algorithm is programmed to identify one or more lesions or other abnormalities of the brain of the subject based on the comparison of voxels of the plurality of anatomical images to corresponding voxels of the plurality of atlas images and to use the identified lesions or other abnormalities as the one or more regions in the plurality of anatomical images to be excluded from atlas registration of the plurality of anatomical images.

15. A non-transitory computer readable medium comprising instructions that, when executed by at least one processor, cause the processor to:

receive a plurality of functional images of a brain of the subject;

receive a plurality of anatomical images of the brain of the subject;

define one or more regions in the plurality of anatomical images to be excluded from atlas registration of the plurality of anatomical images;

register the plurality of anatomical images with atlas images by nonlinear atlas registration with the defined one or more regions excluded to generate a warping map;

register the plurality of functional images with atlas images using the warping map to guide the registration; and compute functional connectivity of the brain of the subject using the registered functional images.

16. The non-transitory computer readable medium of claim 15, wherein the instructions further cause the processor to generate a resting state network map of the brain of the subject based on the computed functional connectivity of the brain of the subject.

17. The non-transitory computer readable medium of claim 16, wherein the instructions cause the processor to generate the resting state network map of the brain of the subject by inputting the computed functional connectivity into a neural network trained to estimate class membership for voxels of functional images of the brain to a plurality of resting state networks.

18. The non-transitory computer readable medium of claim 17, wherein the neural network comprises a multilayer perceptron.

19. The non-transitory computer readable medium of claim 15, wherein the instructions cause the processor to define one or more regions to be excluded from atlas registration by executing a searchlight algorithm programmed to compare voxels of the plurality of anatomical images to corresponding voxels of a plurality of atlas images.

20. The non-transitory computer readable medium of claim 19, wherein the searchlight algorithm is programmed to identify one or more lesions or other abnormalities of the brain of the subject based on the comparison of voxels of the plurality of anatomical images to corresponding voxels of the plurality of atlas images and to use the identified lesions or other abnormalities as the one or more regions in the plurality of anatomical images to be excluded from atlas registration of the plurality of anatomical images.

* * * * *